US010456814B2

(12) United States Patent
Ball et al.

(10) Patent No.: US 10,456,814 B2
(45) Date of Patent: *Oct. 29, 2019

(54) METHOD FOR TREATING A SEMICONDUCTOR DEVICE

(71) Applicant: LIFE TECHNOLOGIES CORPORATION, Carlsbad, CA (US)

(72) Inventors: James A. Ball, Ledyard, CT (US); Phil Waggoner, Guilford, CT (US); Scott Parker, East Haven, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/182,429

(22) Filed: Nov. 6, 2018

(65) Prior Publication Data

US 2019/0070640 A1 Mar. 7, 2019

Related U.S. Application Data

(60) Continuation of application No. 15/387,591, filed on Dec. 21, 2016, now Pat. No. 10,137,480, which is a
(Continued)

(51) Int. Cl.
*B08B 9/08* (2006.01)
*B08B 3/08* (2006.01)
(Continued)

(52) U.S. Cl.
CPC .................. *B08B 3/08* (2013.01); *B08B 9/08* (2013.01); *C11D 1/22* (2013.01); *C11D 3/162* (2013.01);
(Continued)

(58) Field of Classification Search
CPC .... B08B 3/08; B08B 9/08; C11D 1/22; C11D 3/162; C11D 3/3418; C11D 3/43;
(Continued)

(56) References Cited

U.S. PATENT DOCUMENTS 4,070,203 A 1/1978 Neisius et al.
4,153,627 A 5/1979 Delbende et al.
(Continued)

FOREIGN PATENT DOCUMENTS

EP 0627500 12/1994
EP 0913181 5/1999
(Continued)

OTHER PUBLICATIONS

Clausen et al., "Chromatographic Characterization of Phosphonate Analog EDTA-Modified Zirconia Support for Biochromatographic Applications," Analytical Chemistry, vol. 70, No. 2, Jan. 15, 1998, 378-385.
(Continued)

*Primary Examiner* — Sharidan Carrillo

(57) ABSTRACT

A method of treating a sensor array including a plurality of sensors and an isolation structure, where a sensor of the plurality of sensors has a sensor pad exposed at a surface of the sensor array and the isolation structure is disposed between the sensor pad and sensor pads of other sensors of the plurality of sensors, comprises exposing the sensor pad and the isolation structure to a non-aqueous organo-silicon solution including an organo-silicon compound and a first non-aqueous carrier; applying an acid solution including an organic acid and a second non-aqueous carrier to the sensor pad; and rinsing the acid solution from the sensor pad and the isolation structure.

19 Claims, 12 Drawing Sheets

Related U.S. Application Data division of application No. 15/079,532, filed on Mar. 24, 2016, now Pat. No. 9,555,451.

(60) Provisional application No. 62/138,537, filed on Mar. 26, 2015.

(51) Int. Cl.

| | |
|---|---|
| *C11D 3/16* | (2006.01) |
| *G01N 27/414* | (2006.01) |
| *C11D 3/34* | (2006.01) |
| *C11D 3/43* | (2006.01) |
| *C11D 1/22* | (2006.01) |
| *C11D 11/00* | (2006.01) |
| *H01L 21/02* | (2006.01) |
| *C11D 7/50* | (2006.01) |
| *C11D 7/34* | (2006.01) |
| *B05D 3/00* | (2006.01) |
| *B05D 5/12* | (2006.01) |

(52) U.S. Cl.
CPC .............. *C11D 3/3418* (2013.01); *C11D 3/43* (2013.01); *C11D 11/0047* (2013.01); *G01N 27/414* (2013.01); *G01N 27/4145* (2013.01); *H01L 21/02057* (2013.01); *B05D 3/00* (2013.01); *B05D 5/12* (2013.01); *C11D 7/34* (2013.01); *C11D 7/5013* (2013.01); *C11D 7/5022* (2013.01); *G01N 27/4148* (2013.01)

(58) Field of Classification Search
CPC ..... C11D 11/0047; C11D 7/34; C11D 7/5013; C11D 7/5022; G01N 27/414; G01N 27/4145; G01N 27/4148; H01L 21/02057
See application file for complete search history.

(56) References Cited

U.S. PATENT DOCUMENTS

| | | |
|---|---|---|
| 4,165,295 A | 8/1979 | Vander |
| 4,395,348 A | 7/1983 | Lee |
| 4,425,384 A | 1/1984 | Brownscombe |
| 4,480,005 A | 10/1984 | Brownscombe |
| 4,491,530 A | 1/1985 | Thomas |
| 4,522,977 A | 6/1985 | Gardner |
| 4,522,978 A | 6/1985 | Gardner |
| 4,532,296 A | 7/1985 | Gardner |
| 4,532,297 A | 7/1985 | Gardner |
| 4,599,401 A | 7/1986 | Koleske |
| 4,618,458 A | 10/1986 | Prillieux et al. |
| 4,626,570 A | 12/1986 | Gardner |
| 4,629,779 A | 12/1986 | Koleske |
| 5,344,967 A | 9/1994 | Schnur et al. |
| 6,087,529 A | 7/2000 | Mathieu et al. |
| 6,294,392 B1 | 9/2001 | Kuhr et al. |
| 6,398,875 B1 | 6/2002 | Cotte et al. |
| 6,903,064 B1 | 6/2005 | Kasturi et al. |
| 7,378,270 B2 | 5/2008 | Azarnia et al. |
| 8,657,966 B2 | 2/2014 | Kalyankar et al. |
| 9,555,451 B2 * | 1/2017 | Ball .............. C11D 3/3418 |
| 10,041,904 B2 * | 8/2018 | Ball ................. G01N 27/4145 |
| 10,137,480 B2 * | 11/2018 | Ball .............. C11D 3/3418 |
| 2002/0032531 A1 * | 3/2002 | Mansky .............. B01J 19/0046 702/21 |
| 2002/0068685 A1 | 6/2002 | Wojtczak et al. |
| 2004/0045578 A1 * | 3/2004 | Jackson ............... B08B 7/0021 134/1.2 |
| 2005/0170512 A1 * | 8/2005 | Rubin ...................... A61L 2/18 436/43 |
| 2006/0205013 A1 | 9/2006 | Shim |
| 2010/0279910 A1 | 11/2010 | Lee |
| 2010/0301398 A1 | 12/2010 | Rothberg et al. |
| 2013/0189158 A1 | 7/2013 | Li et al. |
| 2014/0148358 A1 * | 5/2014 | Li .......................... G01N 1/18 506/9 |
| 2014/0191293 A1 | 7/2014 | Bustillo et al. |
| 2014/0217477 A1 | 8/2014 | Barbee et al. |
| 2014/0272980 A1 | 9/2014 | Ball et al. |
| 2016/0003768 A1 | 1/2016 | Cicero et al. |
| 2016/0061773 A1 | 3/2016 | Ball et al. |
| 2018/0100849 A1 | 4/2018 | Abdolahad |
| 2019/0070640 A1 * | 3/2019 | Ball .............. C11D 3/3418 |

FOREIGN PATENT DOCUMENTS

| | | |
|---|---|---|
| JP | 2003/046540 | 6/2003 |
| JP | 2007-047025 | 2/2007 |
| JP | 2011-084660 | 4/2011 |
| WO | 2004/083843 | 9/2004 |
| WO | 2012/024500 | 2/2012 |
| WO | 2014/160962 | 10/2014 |

OTHER PUBLICATIONS

Hu et al., "Synthesis and Characterization of New Zirconia-Based Polymerication-Exchange Stationary Phases for High-Performance Liquid Chromatography of Proteins," Analytical Chemistry, vol. 70, No. 9, Mar. 1998, 1934-1942.
Kuo et al., "Field-effect transistor with polyaniline think film as semiconductor,"Synthetic Metals, vol. 88, 1997, 23-30.
Nawrocki et al., "Chemistry of Zirconia and its use in Chromatography," Journal of Chromatography A., vol. 657, 1993, 229-282.
Nawrocki et al, "Part I: Chromatography using ultra-stable metal oxide-based stationary phases for HPLC", Journal of Chromatgraphy A., vol. 1028, 2004, 1-30.
Nawrocki et al, "Part II: Chromatography using ultra-stable metal oxide-based stationary phases for HPLC", Journal of Chromatgraphy A., vol. 1028, 2004, 31-62.
Nawrocki et al., "New Materials for Biotechnology: Chromatographic Stationary Phases Based on Zirconia," Biotechnology Progress, vol. 10, No. 6, 1994, 561-573.
PCT/US2016/024013, "International Search Report and Written Opinion of the International Searching Authority" dated Jun. 14, 2016, 1-12.

* cited by examiner

METHOD FOR TREATING A SEMICONDUCTOR DEVICE

CROSS-REFERENCE TO RELATED APPLICATION(S)

This application is a continuation of U.S. application Ser. No. 15/387,591 filed Dec. 21, 2016 (now U.S. Pat. No. 10,137,480), which is a divisional of U.S. application Ser. No. 15/079,532 filed Mar. 24, 2016 (now U.S. Pat. No. 9,555,451), which claims benefit of U.S. Provisional Application No. 62/138,537 filed Mar. 26, 2015, which are incorporated herein by reference in their entirety.

NOTICE OF INCLUSION OF A COPYRIGHT OR MASK WORK NOTICE

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

FIELD OF THE DISCLOSURE

This disclosure, in general, relates to methods for treating sensor arrays, sensor arrays formed by such methods, and solutions for use in such methods.

BACKGROUND

Arrays of sensors formed in semiconductor substrates are increasingly being used in fields such as analytical chemistry and molecular biology. For example, when analytes are captured on or near sensor pads of a sensor array, the analytes or byproducts of reactions associated with the analytes can be detected and used to elucidate information regarding the analyte. In particular, such sensor arrays have found use in genetic analysis, such as genetic sequencing or quantitative amplification.

During manufacture, various semiconductor processing techniques can alter the nature of the surface of a sensor array and the surface of well structures around the sensor array. Such processing can also leave residues on the surface. Altered surface chemistry or residues can prevent or limit the capture of analytes proximate to the sensors. As such, the effectiveness of such sensor arrays is reduced, and signals resulting from such sensor arrays may include erroneous data or no data.

SUMMARY

In an aspect, a sensor device including a sensor array and optionally an isolation structure, such as a well array, corresponding to the sensor array or a lid attached over the sensor array can be treated with a treatment solution. The treatment solution can include an organic solvent, an organic acid, and an organo-silicon compound. Alternatively, the sensor array can be exposed to an organo-silicon solution including the organo-silicon compound and a non-aqueous carrier, followed by application of an acid solution including the organic acid and a non-aqueous carrier. The sensor device can be further treated with a basic solution, such as a NaOH solution, or can be rinsed with a low boiling organic solvent or water. Optionally, the sensor device can be dried.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
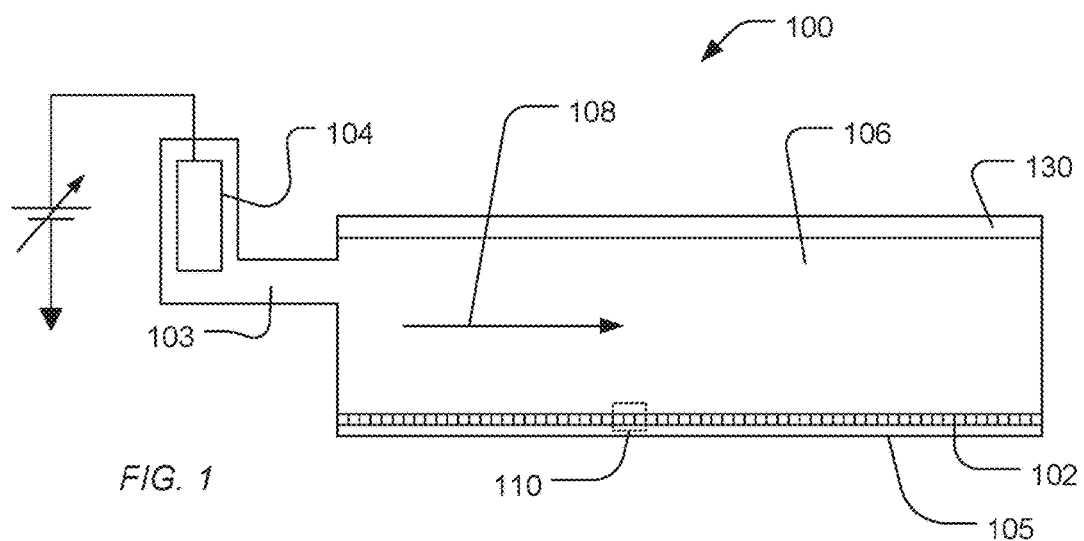
FIG. 1 includes an illustration of an exemplary measurement system.

In an exemplary embodiment, a method for treating a sensor array includes applying a treatment solution to the sensor array and rinsing the treatment solution from the sensor array. In particular, the treatment solution can include an organic solvent, an organic acid, and an organo-silicon compound. Alternatively, the sensor array can be exposed to an organo-silicon solution including the organo-silicon compound and a non-aqueous carrier, followed by application of an acid solution including the organic acid and a non-aqueous carrier. The organo-silicon compound can be a silane, siloxane, or silazane compound, derivative thereof, or any combination thereof. The organo-silicon compound can include a termination moiety, such as an alkyl, vinyl, or hydride moiety, or any combination thereof. The acid can be a sulfonic acid, such as an alkyl or alkyl aryl sulfonic acid. In an example, the alkyl or alkyl aryl sulfonic acid can have an alkyl group having between 9 and 18 carbons. For example, the sulfonic acid can include dodecyl benzene sulfonic acid (DBSA). The organic solvent or the non-aqueous carrier can be a non-polar solvent or an aprotic polar solvent. In an example, the organic solvent can have a normal boiling point a range of 65° C. to 275° C. In an example, the organic solvent includes heptane. In another example, the organic solvent includes undecane.

Following treatment with the treatment solution, the sensor array can be rinsed with a rinse solution. In an example, the rinse solution includes a low boiling organic solvent such as alcohol, for example, ethanol or isopropanol. In another example, the rinse solution can include water. The method can further include applying a basic solution or a weak acid solution following application of the treatment solution and before rinsing. The basic solution can have a pH of greater than 7, such as at least 8, but generally not greater than 14, and can include a strong base, such as sodium hydroxide. In an example, the treatment solution and the basic solution can be applied repeatedly, such as 2 or more times, 3 or more times or even 4 or more times, but generally not greater than 10 times.

In a particular embodiment, a treatment solution is applied to at least a sensor pad of the sensor array. The sensor array can include a plurality of sensors. A sensor of the sensor array can include a sensor pad. Optionally, a well structure can be defined over the sensor array and include a plurality of wells correspond with sensor pads of the sensor array. A well of the well array can expose a sensor pad of a sensor. Optionally, a lid including at least one fluid port can be disposed or attached over the sensor array and the well structure. A space for fluid can be defined between the lid and the well structure or sensor array and can be in fluid communication with the fluid port of the lid. The treatment solution can be applied through the fluid port and into the space between the lid and the well structure. Optionally, a basic solution can be applied through the fluid port to the space between the lid and the well structure following application of the treatment solution. Application of the treatment solution followed by the basic solution can be repeated, such as at least twice or even at least 3 times, but generally not greater than 10 times. A rinse solution can be applied through the fluid port, for example, including alcohol or water. Optionally, the system can be dried.

In another exemplary embodiment, a sensor array includes a plurality of sensors. A sensor of the plurality of sensors includes a sensor pad. A well structure is disposed over the sensor array and includes a well array that operatively corresponds with the sensor array. A well of the well array exposes a sensor pad of a sensor. The treatment solution including an organo-silicon compound, an acid, such as a sulfonic acid, and an organic solvent can be applied to the sensor array for a period between 30 seconds and 30 minutes. The sensor array can be rinsed with a rinse solution. In an example, the rinse solution can include a low boiling organic solvent, such as an alcohol. The sensor array can be rinsed one or more times with the low boiling organic solvent. In another example or in addition, the sensor array can be rinsed with water, such as deionized water. The sensor array can be dried and a lid can be attached over the well structure and the sensor array. The lid can include at least one fluid port. A space is defined between the lid and the sensor array or the well structure and is in fluid communication with the fluid port.

In a particular embodiment, a sensor system includes a flow cell in which a sensory array is disposed, includes communication circuitry in electronic communication with the sensory array, and includes containers and fluid controls in fluidic communication with the flow cell. In an example, FIG. 1 illustrates an expanded and cross-sectional view of a flow cell 100 and illustrates a portion of a flow chamber 106. A reagent flow 108 flows across a surface of a well array 102, in which the reagent flow 108 flows over the open ends of wells of the well array 102. The well array 102 and a sensor array 105 together can form an integrated unit forming a lower wall (or floor) of flow cell 100. A reference electrode 104 can be fluidly coupled to flow chamber 106. Further, a flow cell cover 130 encapsulates flow chamber 106 to contain reagent flow 108 within a confined region.

Figure 2:
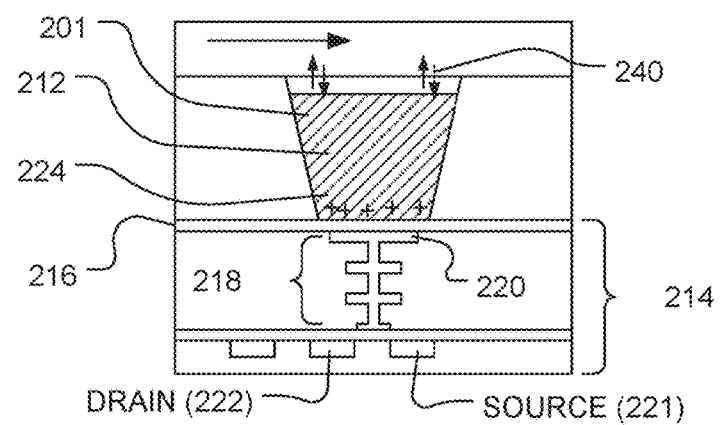
FIG. 2 includes an illustration of an exemplary measurement component.

FIG. 2 illustrates an expanded view of a well 201 and a sensor 214, as illustrated at 110 of FIG. 1. The volume, shape, aspect ratio (such as base width-to-well depth ratio), and other dimensional characteristics of the wells can be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 optionally separated from the well interior by a material layer 216. In addition, a conductive layer (not illustrated) can be disposed over the sensor plate 220. In an example, the material layer 216 includes an ion sensitive material layer. The material layer 216 can be a ceramic layer, such as an oxide of zirconium, hafnium, tantalum, aluminum, or titanium, among others, or a nitride of titanium. In an example, the material layer 216 can have a thickness in a range of 5 nm to 100 nm, such as a range of 10 nm to 70 nm, a range of 15 nm to 65 nm, or even a range of 20 nm to 50 nm. Together, the sensor plate 220 and the material layer 216 form a sensor pad.

While the material layer 216 is illustrated as extending beyond the bounds of the illustrated FET component, the material layer 216 can extend along the bottom of the well 201 and optionally along the walls of the well 201. The sensor 214 can be responsive to (and generate an output signal related to) the amount of a charge 224 present on material layer 216 opposite the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, treatment solutions, and other reagents can move in and out of the wells by a diffusion mechanism 240.

In an embodiment, reactions carried out in the well 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, multiple copies of the same analyte can be analyzed in the well 201 at the same time in order to increase the output signal generated. In an embodiment, multiple copies of an analyte can be attached to a solid phase support 212, either before or after deposition into the well 201. In an example, the solid phase support 212 can be a particle, such as a polymeric particle or an inorganic particle. In another example, the solid phase support 212 can be a polymer matrix, such as a hydrophilic polymer matrix, for example, a hydrogel matrix or the like.

The well 201 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 201 can have a characteristic diameter, defined as the square root of 4 times the cross-sectional area (A) divided by Pi (e.g., $sqrt(4*A/\pi)$), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 201 can have a characteristic diameter of at least 0.01 micrometers.

While FIG. 2 illustrates a single-layer wall structure and a single-layer material layer 216, the system can include one or more wall structure layers, one or more conductive layers or one or more material layers. For example, the wall structure can be formed of one or more layers, including an oxide of silicon or TEOS or including a nitride of silicon.

Figure 3:
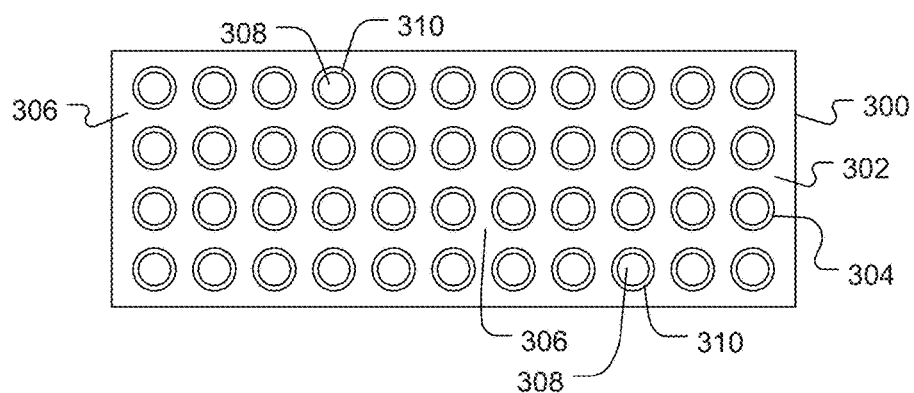
FIG. 3 includes an illustration of exemplary array of measurement components.

In a particular example illustrated in FIG. 3, a system 300 includes a well wall structure 302 defining an array of wells 304 disposed over or operatively coupled to sensor pads of a sensor array. The well wall structure 302 defines an upper surface 306. A lower surface 308 associated with the well is disposed over a sensor pad of the sensor array. The well wall structure 302 defines a sidewall 310 between the upper surface 306 and the lower surface 308. As described above, a material layer in contact with sensor pads of the sensor array can extend along the lower surface 308 of a well of the array of wells 304 or along at least a portion of the wall 310 defined by the well wall structure 302. The upper surface 306 can be free of the material layer. In some examples, at least a portion of the well wall structure 302 is not covered by the material layer.

Figure 4:
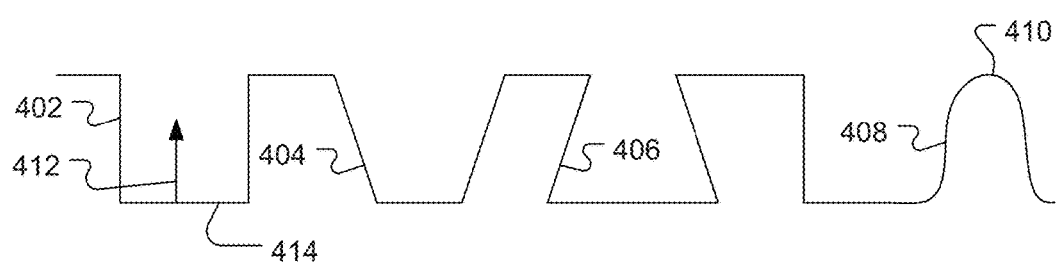
FIG. 4 includes an illustration of exemplary well configurations.

While the wall surface of FIG. 2 is illustrated as extending substantially vertically and outwardly, the wall surface can extend in various directions and have various shapes. Substantially vertically denotes extending in a direction having a component that is normal to the surface defined by the sensor pad. For example, as illustrated in FIG. 4, a well wall 402 can extend vertically, being parallel to a normal component 412 of a surface defined by a sensor pad. In another example, the wall surface 404 extends substantially vertically, in an outward direction away from the sensor pad, providing a larger opening to the well than the area of the lower surface of the well. As illustrated in FIG. 4, the wall surface 404 extends in a direction having a vertical component parallel to the normal component 412 of the surface 414. In an alternative example, a wall surface 406 extends substantially vertically in an inward direction, providing an opening area that is smaller than an area of the lower surface of the well. The wall surface 406 extends in a direction having a component parallel to the normal component 412 of the surface 414.

While the surfaces 402, 404, or 406 are illustrated by straight lines, some semiconductor or CMOS manufacturing processes can result in structures having nonlinear shapes. In particular, wall surfaces, such as wall surface 408 and upper surfaces, such as upper surface 410, can be arcuate in shape or take various nonlinear forms. While the structures and devices illustrated herewith are depicted as having linear layers, surfaces, or shapes, actual layers, surfaces, or shapes resulting from semiconductor processing can differ to some degree, possibly including nonlinear and arcuate variations of the illustrated embodiment.

Figure 5:
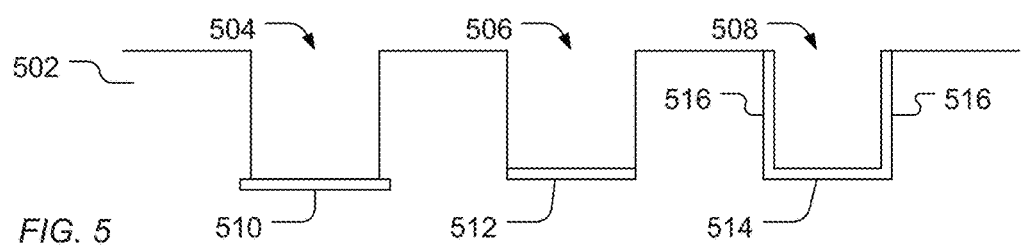
FIG. 5 includes an illustration of exemplary well and sensor configurations.

FIG. 5 includes an illustration of exemplary wells including ion sensitive material layers. For example, a well structure 502 can define an array of wells, such as exemplary wells 504, 506, or 508. The wells (504, 506, or 508) can be operatively coupled to an underlying sensor (not illustrated) or linked to such an underlying sensor. Exemplary well 504 includes an ion sensitive material layer 510 defining the bottom of the well 504 and extending into the structure 502. While not illustrated in FIG. 5, a conductive layer, such as a gate, for example, a floating gate of ion sensitive field effect transistor can reside below the ion sensitive material layer 510.

In another example, as illustrated by well 506, an ion sensitive material layer 512 can define the bottom of the well 506 without extending into the structure 502. In a further example, a well 508 can include an ion sensitive layer 514 that extends along at least a portion of a sidewall 516 of the well 508 defined by the structure 502. As above, the ion sensitive material layers 512 or 514 can reside over conductive layers or gates of underlying electronic devices.

Figure 6:
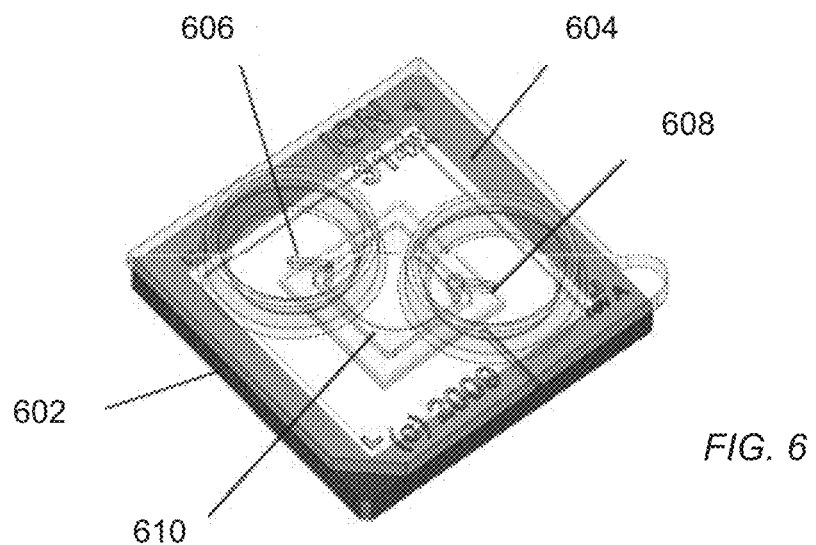
FIG. 6 and FIG. 7 include illustrations of exemplary sensor devices.
Figure 7:
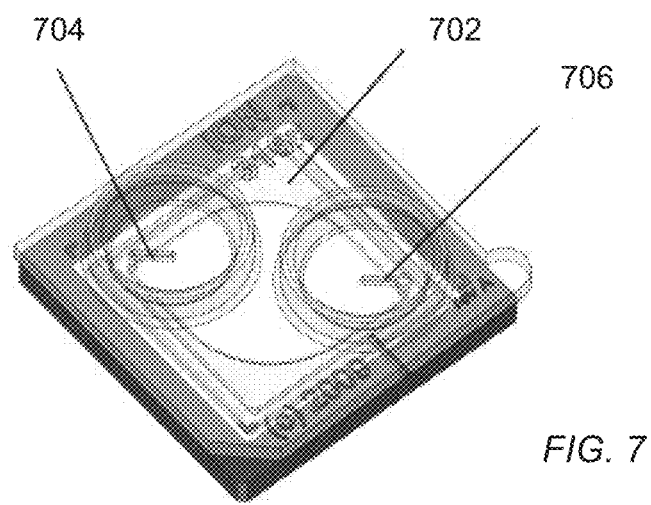

As illustrated in FIG. 6, the sensor device can include a sensor array 602 formed within a semiconductor substrate. A well structure is defined over the sensor array. A lid 604 is attached to the well structure or the sensor array 602. For example, the lid 604 can be adhered to the sensor array or well structure 602 using an adhesive. The lid 604 includes fluid ports 606 or 608, which are in fluid communication with a flow cell 610 defined between the lid 604 and the sensor array and well array 602. Fluid applied to one of the fluid ports 606 or 608 can flow through the flow cell 610 and optionally out the other port 608 or 606. In another example illustrated in FIG. 7, a lid 702 can include fluid ports 704 and 706 and can define a larger flow space. The lid can be adhered over a well array or sensor array, for example, using an adhesive.

Figure 8:
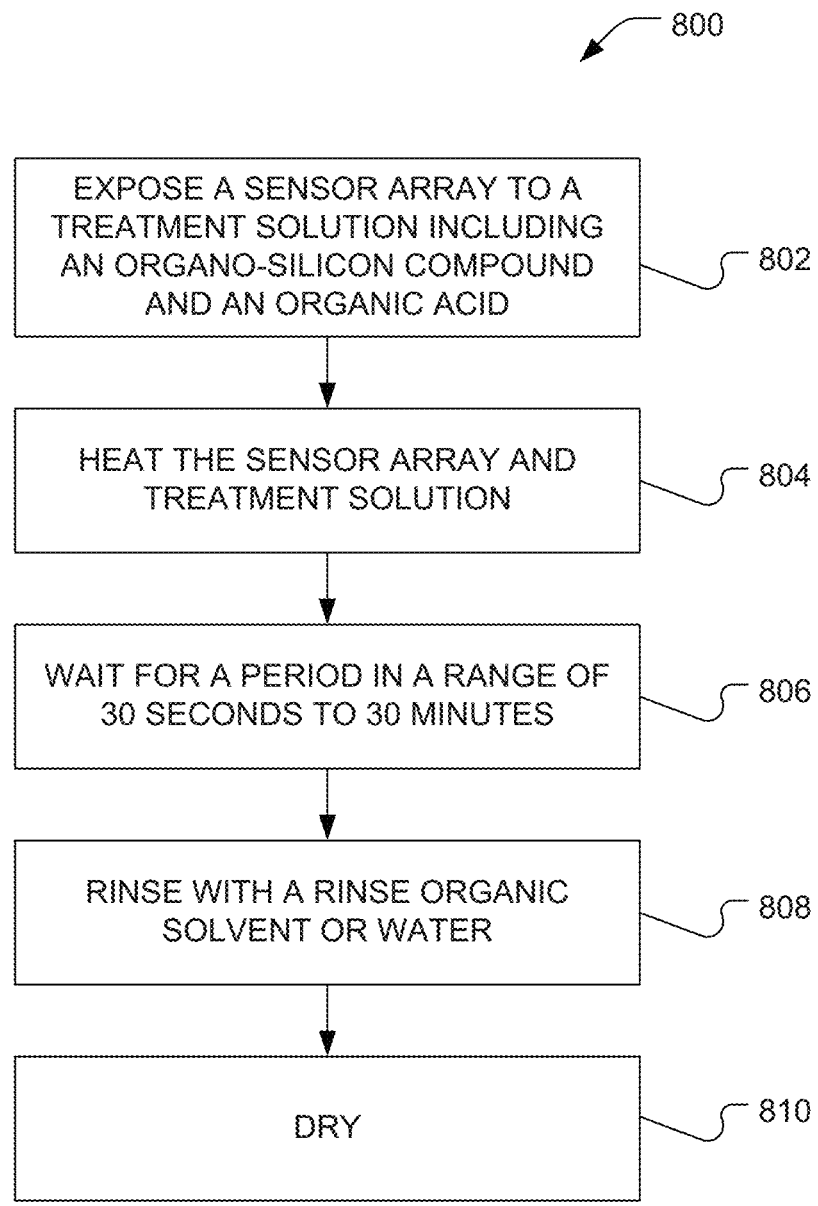
FIG. 8, FIG. 9, FIG. 10, and FIG. 11 include flow diagrams illustrating exemplary methods.

As illustrated in the method 800 of FIG. 8, a sensor array can be exposed to a non-aqueous treatment solution including, an organo-silicon compound and an acid, such as sulfonic acid, phosphonic acid, or a combination thereof, as illustrated 802. The treatment solution can further include an organic solvent.

In an example, the organo-silicon compound can include a silane, a siloxane, a silazane, a derivative thereof, or a combination thereof. In an example, the organo-silicon compound can include a siloxane, such as a polydialkyl siloxane. In another example, the organo-silicon compound can include a polysilazane or a cyclic silazane. Further, the organo-silicon compound can include a terminal moiety, such as an alkyl, vinyl, halyl, sulfonyl, hydroxyl, or hydride moiety, or any combination thereof.

An exemplary silane includes a silane functionalized with a moiety, such as an aryl, polyaryl, alkyl, alkoxyl, halyl, or cyano moiety, or any combination thereof. For example, the silane can include phenyldimethylchlorosilane, tert-butylchlorodiiphenylsilane, chlorotripropylsilane, (N,N-dimethylamino) trimethyl-silane, tris(trimethylsilyl)silane, triethylchlorosilane, 3-cyanopropyldimethylchloro-silane, chlorotriethylsilane, 1,2-bis(chlorodimethylsiyl)ethane, trimethylsilyltrifluoronesulfonate, trioctylsilane, dodecyldimethylchlorosilane, chlorodimethylthexylsilane, trimethylchlorosilane, chloro(chloromethyl) dimethylsilane, thexyldimethylchlorosilane, triisopropylchlorosilane, trimethylmethoxysilane, trimethylchlorosilane, chlorotriisopropylsilane, acetoxytrimethylsilane, or a combination thereof.

In an example, the organo-silicon compound includes a siloxane, such as a polysiloxane, for example, including, aryl, dialkyl or alkylhydro units, or combinations thereof. The alkyl moieties of the dialkyl or alkylhydro units can include methyl, ethyl, propyl, butyl moieties, or any combination thereof. The aryl units can include a phenylalkyl siloxyl unit, such as a phenylmethyl siloxyl unit. The polysiloxane can include a terminal moiety, such as an alkyl, vinyl, halyl, sulfonyl, hydroxyl, or hydride moiety, or any combination thereof. For example, the terminal moiety can include an alkyl, vinyl, hydroxyl, or hydride moiety, or a combination thereof. In particular, the terminal moiety can include an alkyl, vinyl, or hydride moiety. An exemplary alkyl terminal moiety can include a methyl, ethyl, propyl or butyl terminal moiety.

In particular, an exemplary siloxane includes an alkyl terminated polydimethylsiloxane (PDMS), a hydride-terminated polydimethylsiloxane (PDMS), a monovinyl terminated polydimethylsiloxane (PDMS), dichloro-tetramethyldisiloxane, hexamethyltrisiloxane, polymethylhydrosiloxane, tris(trimethylsilyloxy)silane, octamethyltrisiloxane, or a combination thereof. For example, the siloxane can include methyl terminated polydimethylsiloxane (e.g. A, below, where "n" is between 1 and 100, such as between 2 and 50, or between 2 and 20), a vinyl terminated polydimethylsiloxane (e.g., B, below, wherein "n" is between 1 and 100, such as between 2 and 50, or between 2 and 20), a poly dimethyl methylhydro siloxane (e.g., C, below, wherein "m" is between 1 and 100, such as between 2 and 50, or between 2 and 20, and "n" is between 1 and 100, such as between 2 and 50, or between 2 and 20), a butyl terminated polydimethylsiloxane (e.g., D, below, wherein "n" is between 1 and 100, such as between 2 and 50, or between 2 and 20), or a combination thereof.

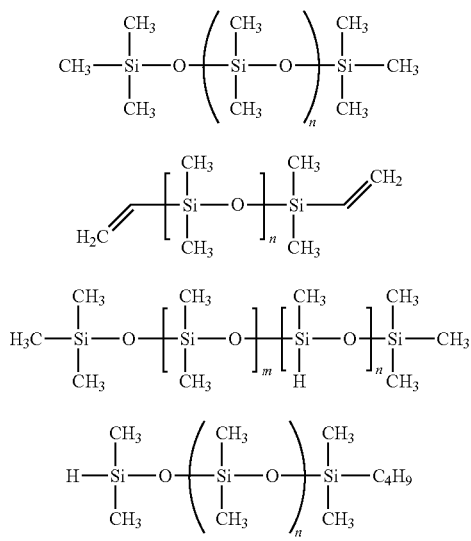

In another example, a siloxane has the formula E below, wherein R can include a hydrophilic, polar, or amphiphilic moiety, or a combination thereof. For example, R can include a polyalkylene oxide moiety. In another example, R can include pyrrolidone functionality. In a further example, R can include a furan moiety. In an additional example, R can include a cyanoalkyl functionality. In another example, R can include an isostearyl alcohol moiety.

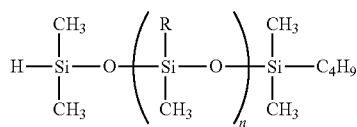

An exemplary silazane includes hexamethylcyclotrisilazane.

In a particular example, the organo-silicon compound has a molecular weight in a range of 50 Da to 10000 Da. For example, the molecular weight can be in a range of 100 Da to 8000 Da, such as a range of 500 Da to 7000 Da, a range of 700 Da to 6000 Da, a range of 900 Da to 6000 Da, or a range of 1200 Da to 6000 Da. In an example, the organo-silicon compound includes a polydimethylsiloxane having a molecular weight in a range 100 Da to 8000 Da, such as a range of 500 Da to 7000 Da, a range of 700 Da to 6000 Da, a range of 900 Da to 6000 Da, or a range of 1200 Da to 6000 Da.

The organo-silicon compound can be included in the treatment solution in an amount in a range of 0.001% to 10.0% by weight. For example, the organo-silicon compound can be included in a range of 0.005% to 10.0%, such as a range of 0.005% to 5.0%, a range of 0.01% to 5.0%, a range of 0.5% to 2.0%, or a range of 0.5% to 1.0% by weight.

The treatment solution can also include a platinum compound, such as a platinum ligand compound. In an example, the ligand can be a vinyl terminated cyclic siloxane, such as cyclic tetra (methylvinyl siloxane). In a particular example, the platinum compound has the configuration F below. The treatment solution can include the platinum compound in an amount in a range of 0.0005% to 1.0% by weight, such as a range of 0.005% to 0.5% or a range of 0.01% to 0.1% by weight.

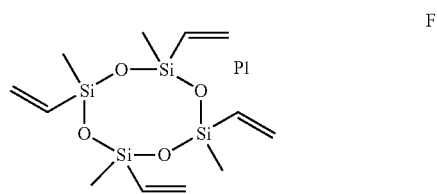 [SMILES: C=C[Si]1(C)O[Si](C)(C=C)O[Si](C)(C=C)O[Si](C)(C=C)O1]

An exemplary sulfonic acid includes an alkyl sulfonic acid, an alkyl aryl sulfonic acid, or a combination thereof. An exemplary alkyl sulfonic acid includes an alkyl group having 1 to 18 carbons, such as 1 to 14 carbons, 1 to 10 carbons, or 1 to 5 carbons. In another example, the alkyl group of the alkyl sulfonic acid has 10 to 14 carbons. For example, an alkyl sulfonic acid can include methanesulfonic acid, ethanesulfonic acid, propane sulfonic acid, butane sulfonic acid, or combinations thereof. In another example, the alkyl group can be functionalized, for example, with a terminal functional group opposite the sulfonic acid functional group. An exemplary functionalized alkyl sulfonic acid includes an alkyl sulfonic acid functionalized with a terminal amine group, such as taurine. In a further example, the alkyl groups of the sulfonic acid can be halogenated, such as fluorinated.

In a further example, the sulfonic acid includes an alkyl aryl sulfonic acid. The alkyl aryl sulfonic acid, for example, alkyl benzene sulfonic acid, can include an alkyl group having between 1 and 20 carbons. For example, the alkyl group can have between 9 and 18 carbons, such as between 10 and 14 carbons. In a particular example, the alkyl aryl sulfonic acid includes dodecyl benzene sulfonic acid (DBSA). The dodecyl benzene sulfonic acid (DBSA) can be a purified form of dodecyl benzene sulfonic acid having at least 90%, such as at least 95% of alkyl aryl sulfonic acid having an alkyl group with 12 carbons. Alternatively, the dodecyl benzene sulfonic acid can include a blend of alkyl benzene sulfonic acid having alkyl groups with an average of 12 carbons. The alkyl aryl sulfonic acid can be alkylated at a blend of positions along the alkyl chain. In another example, the alkyl group can have between 1 and 6 carbons. For example, the alkyl aryl sulfonic acid can include toluene sulfonic acid.

The treatment solution can have a concentration between 10 mM and 500 mM acid, such as sulfonic acid. For example, the treatment solution can have a concentration between 50 mM and 250 mM acid. In another example, the treatment solution includes between 0.5 wt % and 25 wt % of the acid, such as sulfonic acid. For example, the treatment solution can include between 1 wt % and 10 wt % of the acid, such as between 2.5 wt % and 5 wt % of the acid, such as sulfonic acid.

The organic solvent within the treatment solution is a non-aqueous solvent providing solubility for the acid (e.g., sulfonic acid) to at least the concentrations above. In an example, the organic solvent can be aprotic. The organic solvent can be a non-polar organic solvent. In another example, the organic solvent can be a polar aprotic solvent. In an example, the organic solvent can have a normal boiling point in a range of 36° C. to 345° C. For example, the normal boiling point can be in a range of 65° C. to 275° C. In another example, the normal boiling point can be in a range of 65° C. to 150° C. Alternatively, the normal boiling point is in a range of 150° C. to 220° C.

In a particular example, the non-polar organic solvent includes an alkane solvent, an aromatic solvent, or a combination thereof. An alkane solvent can have between 6 and 20 carbons. For example, the alkane can have between 6 and 14 carbons, such as between 6 and 9 carbons. Alternatively, the alkane can have between 10 and 14 carbons. In a particular example, the alkane is a linear alkane. For example, the alkane solvent can include pentane, hexane, heptanes, octane, decane, undecane, dodecane, or combinations thereof. In another example, the alkane is halogenated. An exemplary branched alkane can include hydrogenated dimers of C11 or C12 alpha olefins.

In a further example, the organic solvent can include a polar aprotic solvent. For example, the polar aprotic solvent can include tetrahydrofuran, ethylacetate, acetone, dimethylformamide, acetonitrile, dimethyl sulfoxide, N-methyl pyrrolidone (NMP), or a combination thereof. In another example, the organic solvent may be free of ether solvents and, for example, may include dimethylformamide, acetonitrile, dimethyl sulfoxide, or a combination thereof.

As illustrated at 804, the treatment solution and sensor device can be heated while the sensor pad is exposed to treatment solution. In an example, the treatment solution and the sensor device can be heated at a temperature in a range of 35° C. to 60° C. For example, the temperature can be in a range of 40° C. to 50° C.

As illustrated 806, the sensor array can be exposed to the treatment solution and optionally heated for a period in a range of 30 seconds to 30 minutes. For example, the period can be in a range of 30 seconds to 10 minutes, such as a range of 30 seconds to 5 minutes, or even a range of 1 minute to 2 minutes.

An organic solvent or water can be used to rinse the sensor array, as illustrated 808, following exposure to the treatment solution. The organic solvent can be a low boiling organic solvent. An exemplary low boiling organic solvent can have a normal boiling point range of 25° C. to 100° C., such as a normal boiling point in a range of 50° C. to 100° C. In an example, the low boiling organic solvent includes an alcohol, such as ethanol or propanol. Alternatively, the organic solvent can be N-methyl pyrrolidone (NMP). Alternatively or in addition, the sensor array can be rinsed with water, such as deionized water. In a particular example, the organic solvent is at least partially miscible with water and the organic solvent of the acid/solvent mixture.

As illustrated at 810, the sensor array can be dried. In an example, the sensor array can be dried under an inert atmosphere, such as using dry nitrogen or helium. In another example, the sensor can be heated under a dry atmosphere. In a further example, the sensor array can be dried under vacuum.

Figure 9:
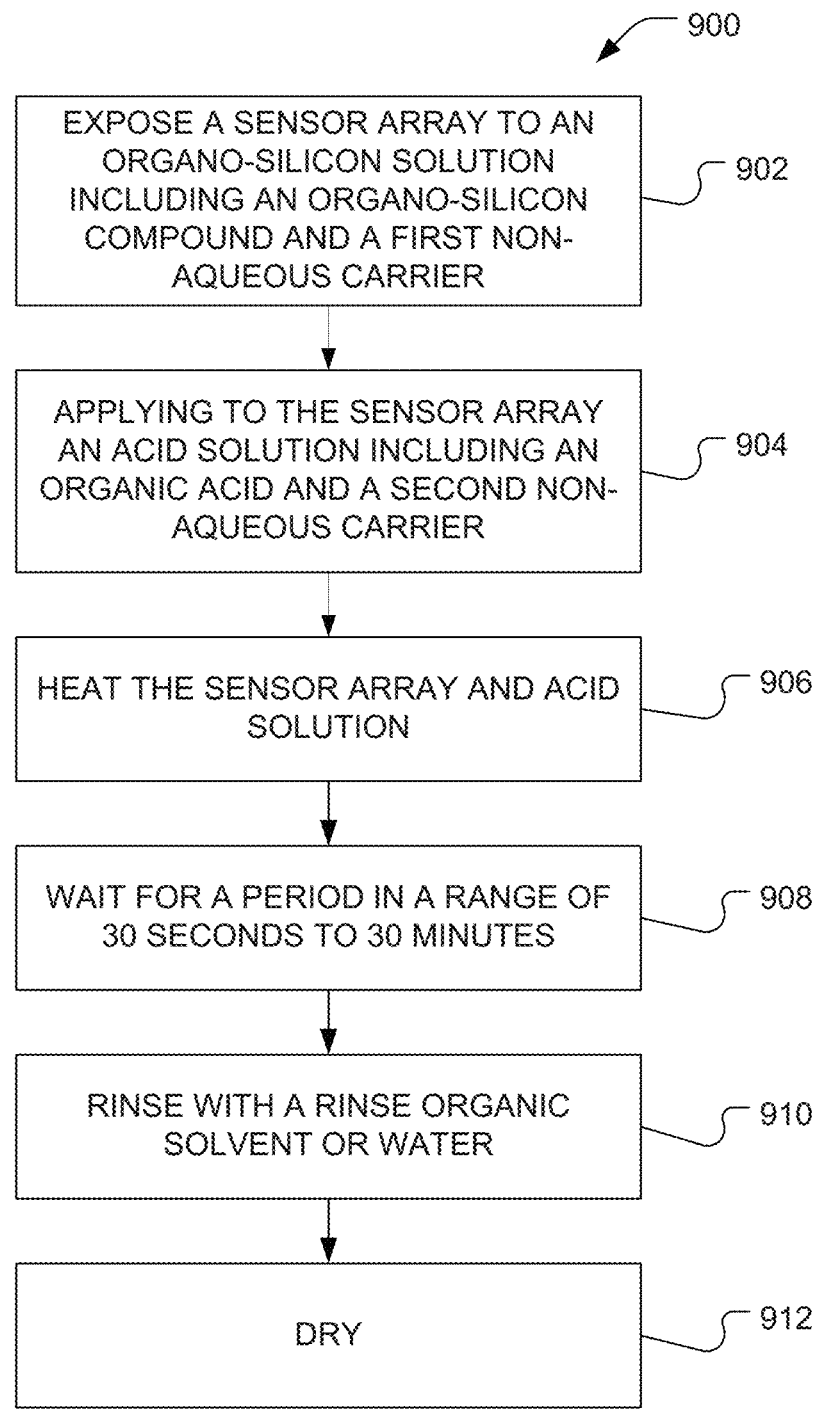

In another example illustrated in FIG. 9, a method 900 for treating a sensor array includes exposing the sensor array to an organo-silicon solution followed by applying an acid solution to the sensor array. For example, as illustrated at 902, the sensor array is exposed to an organo-silicon solution that includes an organo-silicon compound and a non-aqueous carrier. In an example, the organo-silicon compound can be selected from the organo-silicon compounds described above. In a particular example, the organo-silicon compound is a polyalkylsiloxane or a polyalkyl hydroalkylsiloxane. The non-aqueous carrier can be selected from the organic solvents described above. For example, the non-aqueous carrier can be an aprotic or non-polar solvent as described above. In a particular example, the non-aqueous carrier can be an alkane, such as undecane.

As illustrated at 904, an acid solution can be applied to the sensor array. In an example, the acid solution includes an organic acid, such as the acids described above. The acid solution can also include a non-aqueous carrier, for example, selected from the organic solvents described above. For example, the non-aqueous carrier can be an aprotic or non-polar solvent as described above. In a particular example, the non-aqueous carrier can be an alkane, such as undecane. Optionally, the non-aqueous carrier of the organo-silicon solution can be the same as the non-aqueous carrier of the acid solution. Alternatively, the non-aqueous carriers are different.

The method 900 can further include heating the sensor in the presence of the acid solution, as illustrated at 906, waiting for a period, as illustrated at 908, rinsing, as illustrated at 910, and optionally drying, as illustrated at 912, in a manner similar to that described above in relation to FIG. 8 (804-810). The exposing to the organo-silicon solution (902) and applying the acid solution (904) can be repeated prior to drying.

Figure 10:
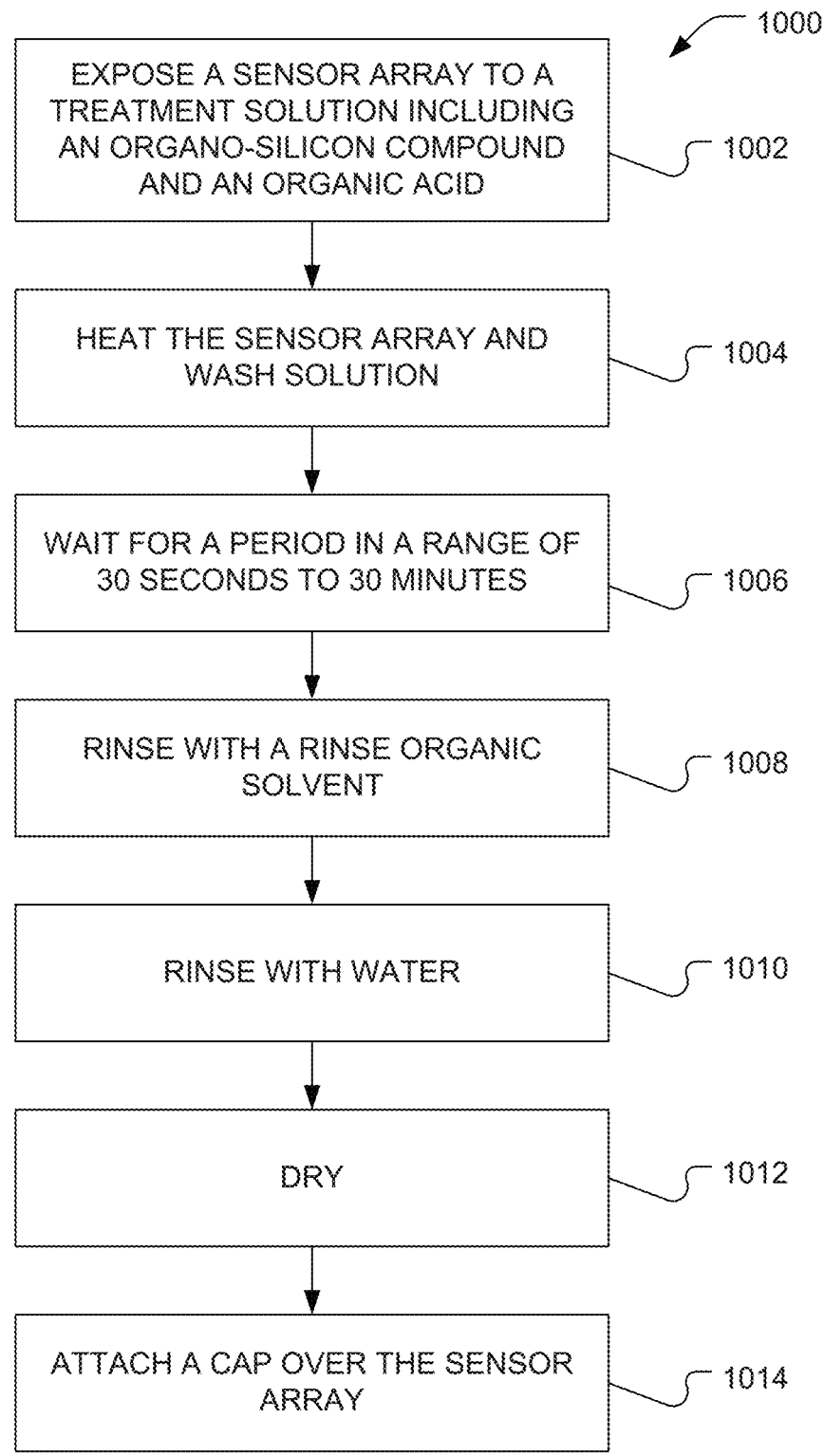

In a further example illustrated in FIG. 10, a method 1000 includes exposing a sensor array to a treatment solution including organo-silicon compound and an acid, for example, as described above, as illustrated at 1002. A sensor device can include the sensor array and optionally a well structure defining a well array operatively corresponding to the sensor array. A well of the well array can expose a sensor pad of a sensor of the sensor array. The treatment solution can have the composition described above. Optionally, the sensor array and the treatment solution can be heated, as illustrated at 1004. For example, the sensor array and the treatment solution can be heated to temperatures described above.

In a further example, the sensor array can be exposed to the treatment solution and optionally heated for a period in a range of 30 seconds to 30 minutes, as illustrated at 1006. Alternatively, the sensor array can be exposed to a treatment solution and optionally heated for the time periods described above.

Following exposure to the treatment solution, the sensor array can be rinsed with a solvent, e.g., a low boiling solvent, as illustrated at 1008. Exemplary low boiling solvents are described above. Alternatively, the solvent can be N-methyl pyrrolidone (NMP). The sensor array can be rinsed with the low boiling solvent one time or more than one time.

Following rinsing with the low boiling organic solvent, the sensor array can be rinsed with water, such as deionized water, as illustrated at 1010. Following rinsing with water, the sensor array can be dried, as illustrated at 1012. For example, the sensor array can be exposed to dry nitrogen gas.

Once dried, a lid can be applied over the sensor array, as illustrated at 1014. For example, the lid can be attached to the sensor array or an intervening well structure using an adhesive. In particular, the lid includes fluid ports in fluid communication with a space defined between the lid and a well structure over the sensor array. Optionally, the method can be applied to a wafer prior to separating the wafer into arrays and capping individual arrays.

Figure 11:
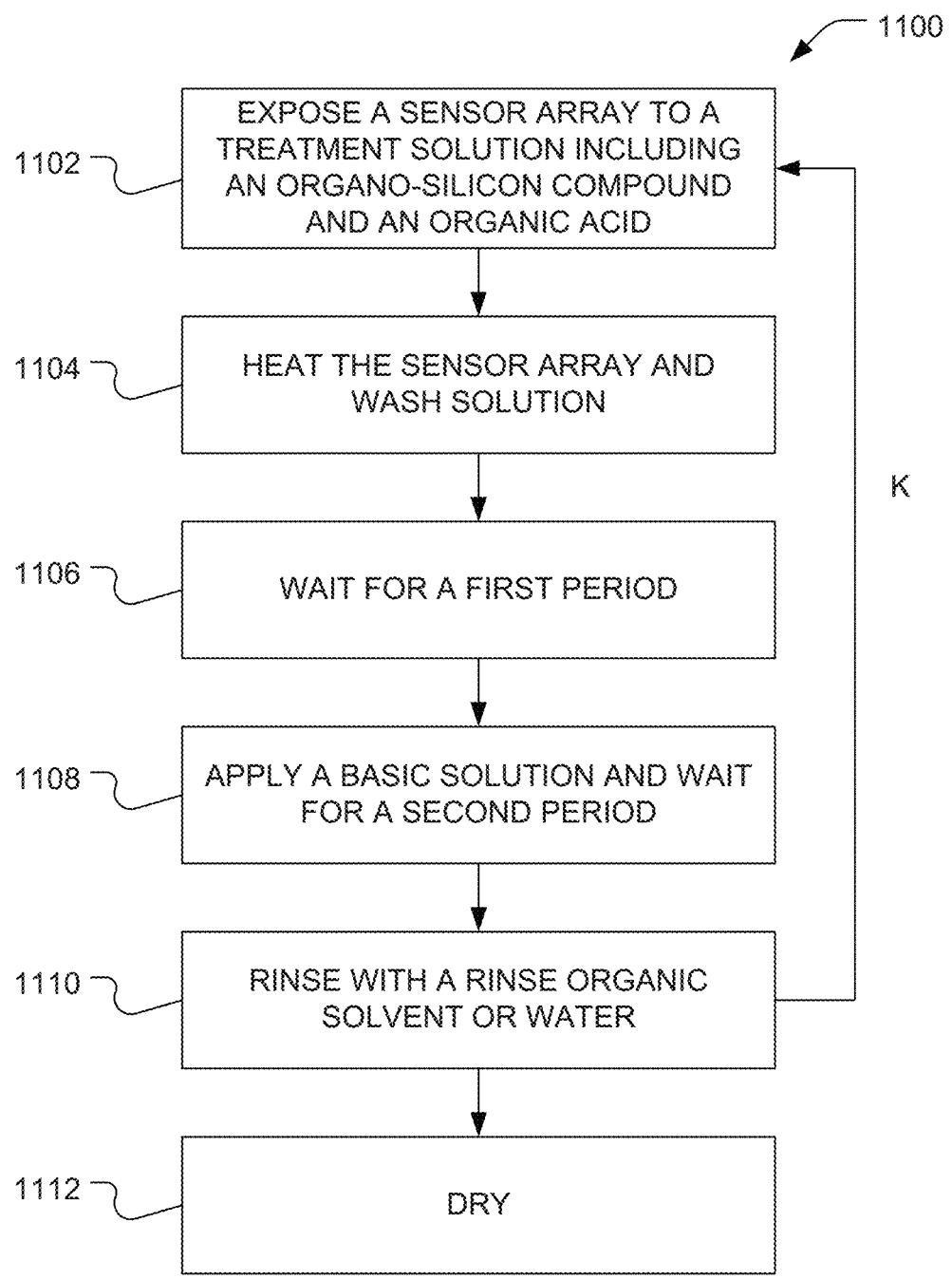

In a further exemplary embodiment illustrated in FIG. 11, a method 1100 includes exposing a sensor array to a treatment solution that includes an organo-silicon compound and an acid, as illustrated at 1102. The treatment solution can further include an organic solvent. In particular, the sensor array can include a well structure defining an array of wells operatively corresponding to the array of sensors. A sensor pad of a sensor is exposed by a well of the well array. A lid can be attached over the sensor array or the well array. The lid includes fluid ports in communication with a space defined between the lid and the well array or sensor array. The treatment solution can be applied through the fluid port into the space. The composition of a treatment solution can be as described above.

Optionally, as illustrated at 1104, the treatment solution and the sensor array can be heated. For example, the treatment solution and the sensor array can be heated at the temperatures described above.

The sensor array can be exposed to the treatment solution and optionally heated for a first period, as illustrated at 1106. The first period can have a range of 30 seconds to 30 minutes, such as the ranges of times periods described above.

In addition, a basic solution can be applied to the sensor array for a second period, as illustrated at 1108. For example, the basic solution can be applied through a fluid port of a lid and into the space defined between the lid and the well structure or sensor array. The basic solution has a pH greater than 7, such as a pH greater than 8, or even a pH greater than 9, but generally not greater than 14. The basic solution includes a strong base, such as sodium or potassium hydroxide or a tetraalkyl ammonium hydroxide, such as tetramethyl ammonium hydroxide or tetraethyl ammonium hydroxide. The base is in a concentration between 0.05 M and 1.5 M. For example, the base can be in a concentration between 0.05 M and 1.0 M, such as between 0.05 M and 0.5 M. The sensor array can be exposed to the basic solution for a period of between 20 seconds and 15 minutes, such as a period of between 20 seconds and 5 minutes or a period of between 30 seconds and 2 minutes. Alternatively, a weak acid solution can be substituted for the basic solution.

The sensor array can be exposed to the treatment solution followed by exposure to the basic solution or the weak acid repeatedly, such as k times. For example, k can be 1, 2, or 3, but generally is not greater than 10. Optionally, the organo-silicon compound can be included in the treatment solution for the first treatment cycle, but not subsequent treatment cycles. Alternatively, the organo-silicon compound can be included in the last treatment cycle, but not prior treatment cycles. In a further example, the organo-silicon compound can be included in each of the repeated treatment cycles, or a subset of the treatment cycles.

Following exposure to the treatment solution and the basic solution, the sensor array can be rinsed with the organic solvent or water, as illustrated at 1110. Exemplary low boiling organic solvents include those described above. Alternatively, the organic solvent can be N-methyl pyrrolidone (NMP). The sensor array can be rinsed with low boiling organic solvents one or more times, optionally followed by a rinse with water between the solvent rinses. Optionally, the sensor array can be dried, such as with exposure to dry nitrogen, as illustrated at 1112.

The method of FIG. 11 can alternatively be applied to a wafer including multiple arrays. The wafer can be separated into individual arrays and lids applied to the individual arrays following drying the wafer.

Such treatment of sensor arrays has been shown to improve loading of polymeric beads that incorporating an analyte and secure the analyte in proximity to sensor pads of the sensor array. In particular, such treatment improves loading of polymeric beads that include polynucleotide analytes amplified thereon. For example, such treatment methods improve the performance of sequence sequencing devices. Such treatment of sensor arrays has been shown to improve sensor signal and signal-to-noise ratio (SNR), particularly in FET-based sensor arrays.

Figure 12:
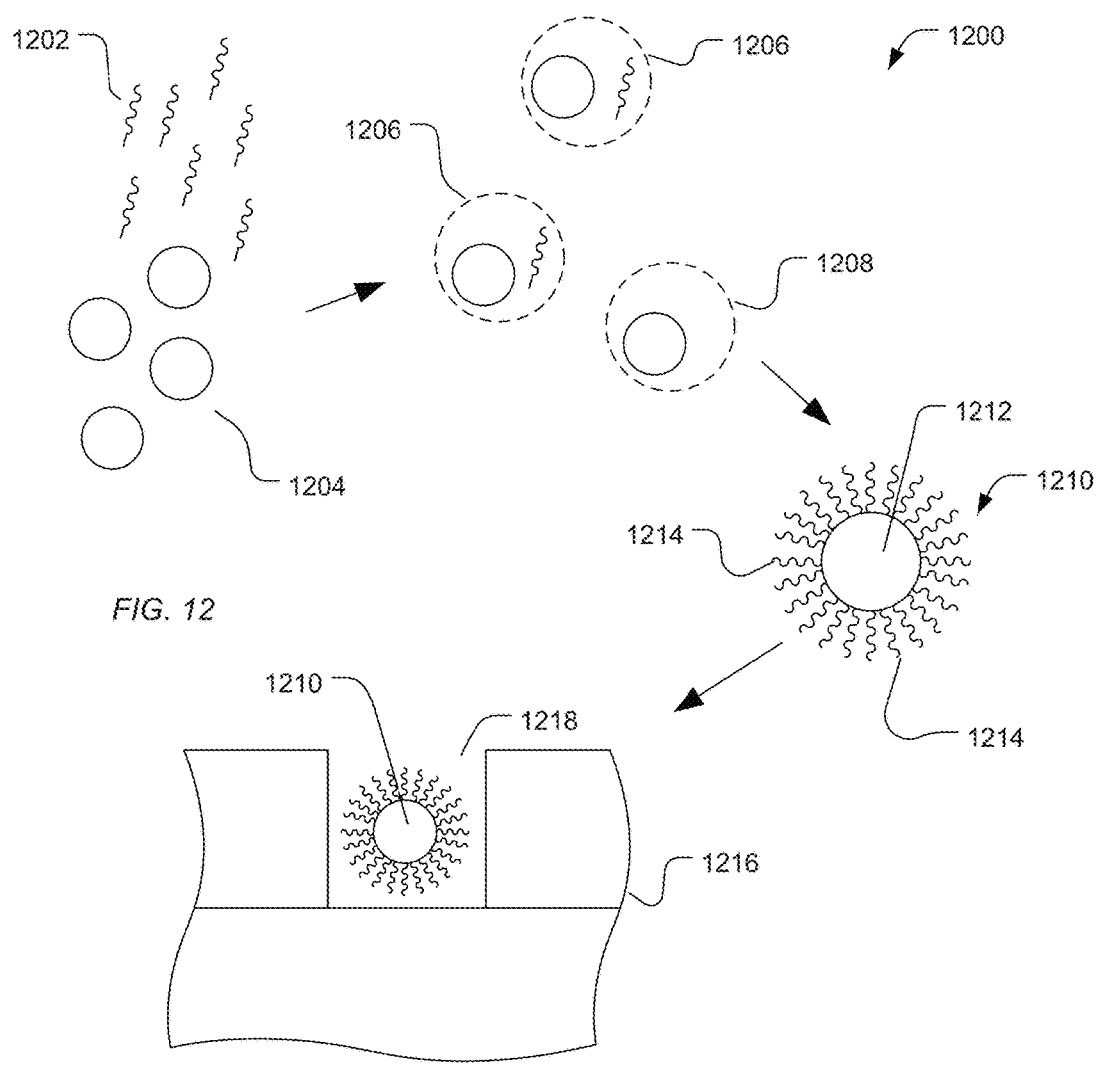
FIG. 12 includes an illustration of exemplary methods for preparing a sequencing device.

For example, FIG. 12 illustrates and exemplary sequencing system enhanced by the above described treatment methods. In a particular example illustrated in FIG. 12, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

In general, the polymeric particle can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

As illustrated in FIG. 12, a plurality of polymeric particles 1204 can be placed in a solution along with a plurality of polynucleotides 1202. The plurality of particles 1204 can be activated or otherwise prepared to bind with the polynucleotides 1202. For example, the particles 1204 can include an oligonucleotide complementary to a portion of a polynucleotide of the plurality of polynucleotides 1202. In another example, the polymeric particles 1204 can be modified with target polynucleotides 1204 using techniques such as biotin-streptavidin binding.

In a particular embodiment, the hydrophilic particles and polynucleotides are subjected to polymerase chain reaction (PCR) amplification or recombinase polymerase amplification (RPA). For example, dispersed phase droplets 1206 or 1208 are formed as part of an emulsion and can include a hydrophilic particle or a polynucleotide. In an example, the polynucleotides 1202 and the hydrophilic particles 1204 are provided in low concentrations and ratios relative to each other such that a single polynucleotide 1202 is likely to reside within the same dispersed phase droplets as a single hydrophilic particle 1204. Other droplets, such as a droplet 1208, can include a single hydrophilic particle and no polynucleotide. Each droplet 1206 or 1208 can include enzymes, nucleotides, salts or other components sufficient to facilitate duplication of the polynucleotide.

In a particular embodiment, an enzyme such as a polymerase is present, bound to, or is in close proximity to the hydrophilic particle or hydrogel particle of the dispersed phase droplet. In an example, a polymerase is present in the dispersed phase droplet to facilitate duplication of the polynucleotide. A variety of nucleic acid polymerase may be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

Following PCR or RPA, particles are formed, such as particle 1210, which can include the hydrophilic particle 1212 and a plurality of copies 1214 of the polynucleotide. While the polynucleotides 1214 are illustrated as being on a surface of the particle 1210, the polynucleotides can extend within the particle 1210. Hydrogel and hydrophilic particles having a low concentration of polymer relative to water can include polynucleotide segments on the interior of and throughout the particle 1210 or polynucleotides can reside in pores and other openings. In particular, the particle 1210 can permit diffusion of enzymes, nucleotides, primers and reaction products used to monitor the reaction. A high number of polynucleotides per particle can produce a better signal.

In embodiments, polymeric particles from an emulsion-breaking procedure can be collected and washed in preparation for sequencing. Collection can be conducted by contacting biotin moieties (e.g., linked to amplified polynucleotide templates which are attached to the polymeric particles) with avidin moieties, and separation away from polymeric particles lacking biotinylated templates. Collected polymeric particles that carry double-stranded template polynucleotides can be denatured to yield single-stranded template polynucleotides for sequencing. Denaturation steps can include treatment with base (e.g., NaOH), formamide, or pyrrolidone.

In an exemplary embodiment, the particle 1210 can be utilized in a sequencing device. For example, a sequencing device 1216 can include an array of wells 1218. The sequencing device 1216 can be treated with a treatment solution including sulfonic acid, as described above. A particle 1210 can be placed within a well 1218.

In an example, a primer can be added to the wells 1218 or the particle 1210 can be pre-exposed to the primer prior to placement in the well 1218. In particular, the particle 1210 can include bound primer. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 1218 to facilitate detectable reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 1216 and can migrate to the well 1218. Excitation energy can be also provided to the well 1218. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 1218 can change. Such a change in pH can be detected by ion sensitive field effect transistors (ISFET). As such, a change in pH can be used to generate a signal indicating the order of nucleotides complementary to the polynucleotide of the particle 1210.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, a FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET array can comprise $10^2$, $10^3$, $10^4$, $10^5$, $10^6$, $10^7$ or more FETs, but generally not more than $10^{12}$.

In embodiments, one or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 12, in another example, a well 1218 of the array of wells can be operatively connected to measuring devices. For example, for fluorescent emission methods, a well 1218 can be operatively coupled to a light detection device. In the case of ionic detection, the lower surface of the well 1218 may be disposed over a sensor pad of an ionic sensor, such as a field effect transistor.

One exemplary system involving sequencing via detection of ionic byproducts of nucleotide incorporation is the Ion Torrent™ PGM™, Proton™, or S5™ sequencer (Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent™ PGM™, Proton™, or S5™ sequencer detects the nucleotide incorporations by detecting the hydrogen ion byproducts of the nucleotide incorporations. The Ion Torrent™ PGM™, Proton™, or S5™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

Embodiments of the above described treatment methods and sensor apparatuses treated using such methods exhibit technical advantages including improved nucleic acid particle loading or signal quality. Improvements in particle loading or signal strength further enhance analysis techniques, such as base-calling and sequencing. It is believed that some technical advantages are derived from activation of organo-silicon compounds, for example, through acid catalyzed breaking of siloxane bonds, which then react with hydroxyl groups associated with the surfaces of metal or semi-metal oxides.

EXAMPLES

Example 1

Organo-silicon compounds are tested for influence on buffering, signal-to-noise, key signal, and Q20 mean using an ION Torrent® Proton I on an ION Torrent® Proton Sequencer. A solution of undecane including 5 wt % dodecyl benzene sulfonic acid and 5 wt % of the selected organo-silicon compound are applied through ports of a Proton I chip and remain in contact with sensor surfaces for approximately 2 minutes. The Proton I chips are flushed with water and isopropyl alcohol. A 5 wt % DBSA in undecane solution is applied through port of the Proton I chip followed by a base solution including 10 mM NaOH. The DBSA and NaOH treatment is repeated three times. The Proton I chip is then flushed with water and isopropyl alcohol.

The Proton I chip is loaded with nucleic acid beads using an ION Chef™ under standard protocols. The Proton I chip is applied to the Proton Sequencer and standard testing is performed to determine buffering, loading, signal-to-noise, key signal, and q20 mean measurements.

The organo-silicon compound is selected from hydride-terminated polydimethylsiloxane, 2,2,4,4,6,6-hexamethylcyclotrisilazane, monovinyl functional polydimethylsiloxane (PDMS), platinum-cyclovinylmethyl siloxane, phenyldimethylchlorosilane, triisopropylsiyl trifluoromethanesulfonate, tert-butylchlorodiiphenylsilane, monohydride terminated PDMS, chlorotripropylsilane, (N,N-dimethylamino) trimethyl-silane, tris(trimethylsilyl)silane, triethylchlorosilane, 3-cyanopropyldimethylchloro-silane, chlorotriethylsilane, hydride-terminated polydimethylsiloxane (PDMS), 1,3-dichloro-1,1,3,3-tetramethyldisiloxane, 1,2-bis(chlorodimethylsiyl)ethane, trimethylsilyltrifluoronesulfonate, trioctylsilane, dodecyldimethylchlorosilane, chlorodimethylthexylsilane, trimethylchlorosilane, hexamethyltrisiloxane, chloro(chloromethyl) dimethylsilane, polymethylhydrosiloxane, thexyldimethylchlorosilane, vinyl terminated PDMS, triisopropylchlorosilane, vinyl terminated PDMS, trimethylmethoxysilane, tris(trimethylsilyloxy)silane, octamethyltrisiloxane, trimethylchlorosilane, chlorotriisopropylsilane, or acetoxytrimethylsilane. Some species of PDMS are also tested in combination with a platinum catalyst, platinum-cyclovinylmethyl siloxane.

Figure 13:
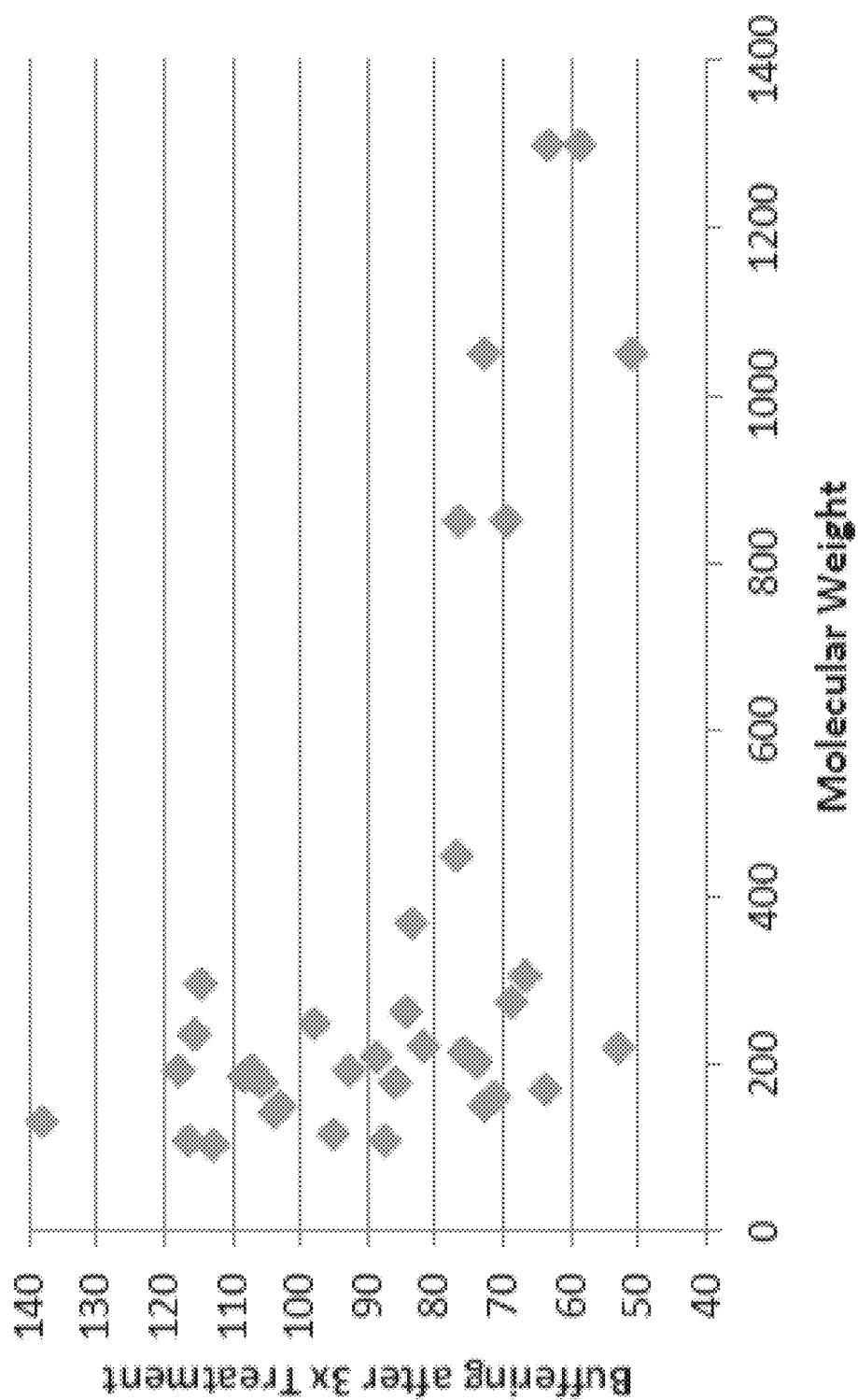
FIG. 13, FIG. 14, FIG. 15, and FIG. 16 include graphs illustrating the influence of organo-silicon compounds on sequencing performance.

As illustrated in FIG. 13, many of the organo-silicon compounds provided desirably low buffering following the three treatments with DBSA and NaOH. Some species provide buffering of less than 100, particularly less than 90, with some species providing buffering in a range of 50 to 80. In particular, higher molecular weight PDMS species provided low buffering and offer additional advantages in easy of handling.

Figure 14:
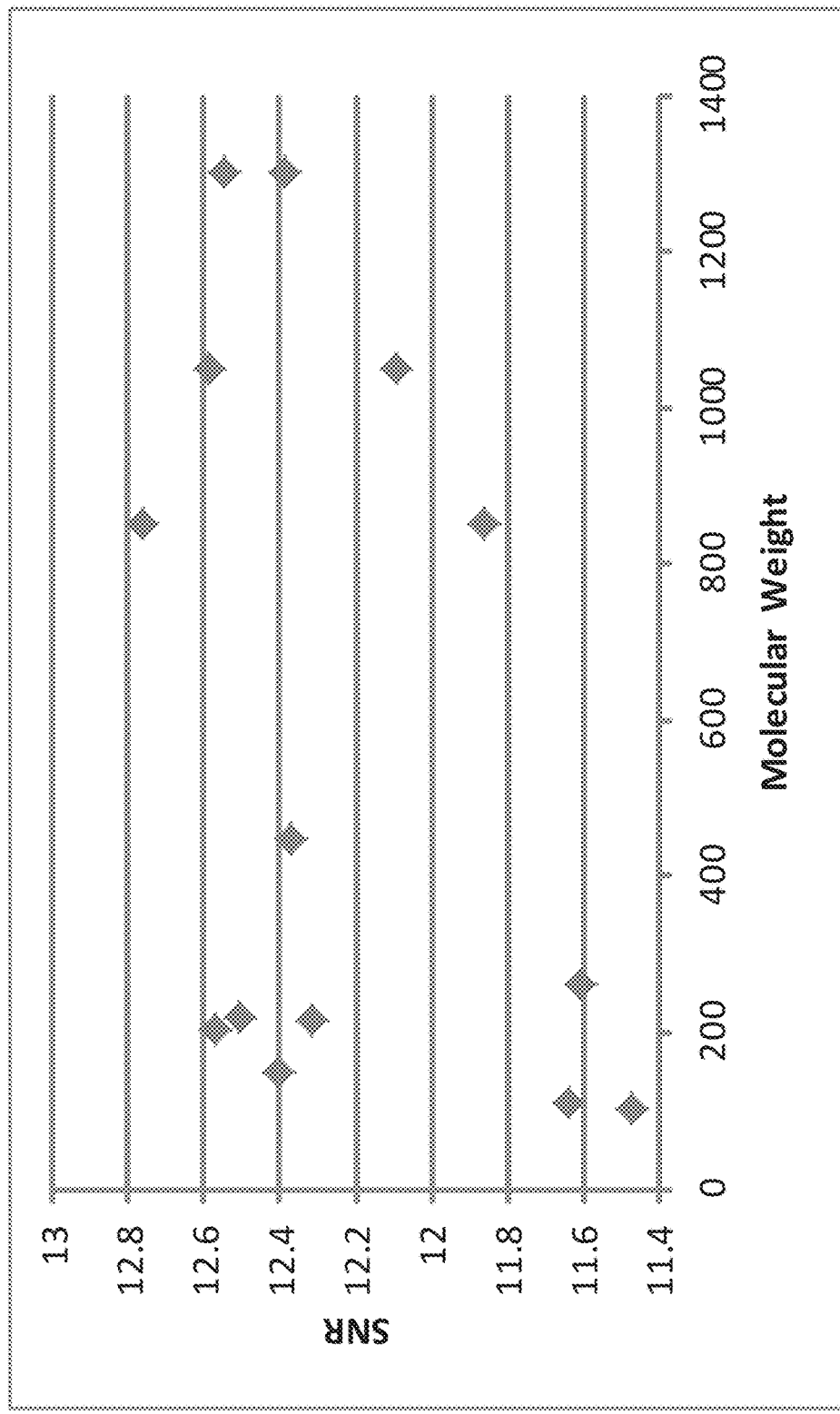
Figure 15:
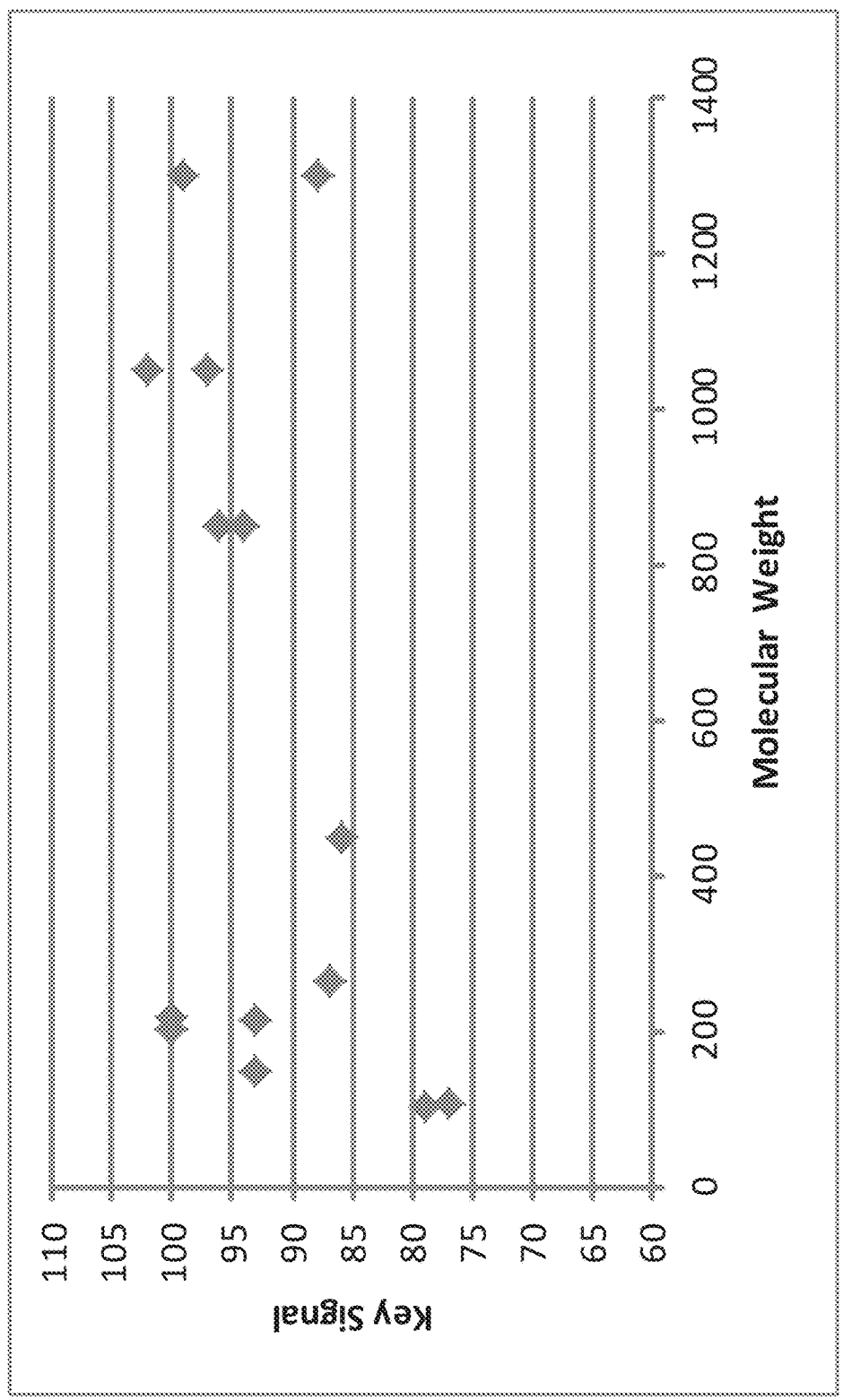

FIG. 14 illustrates signal-to-noise ratios for a subset of species having buffering of less than 100. Several of the high molecular weight PDMS species provide desirable signal-to-noise greater than 12, with some providing a signal-to-noise of greater than 12.3. Such high molecular weight PDMS species also provide desirable key signal of greater than 90, as illustrated in FIG. 15. Other species of organo-silicon compounds also provide desirable key signal.

Figure 16:
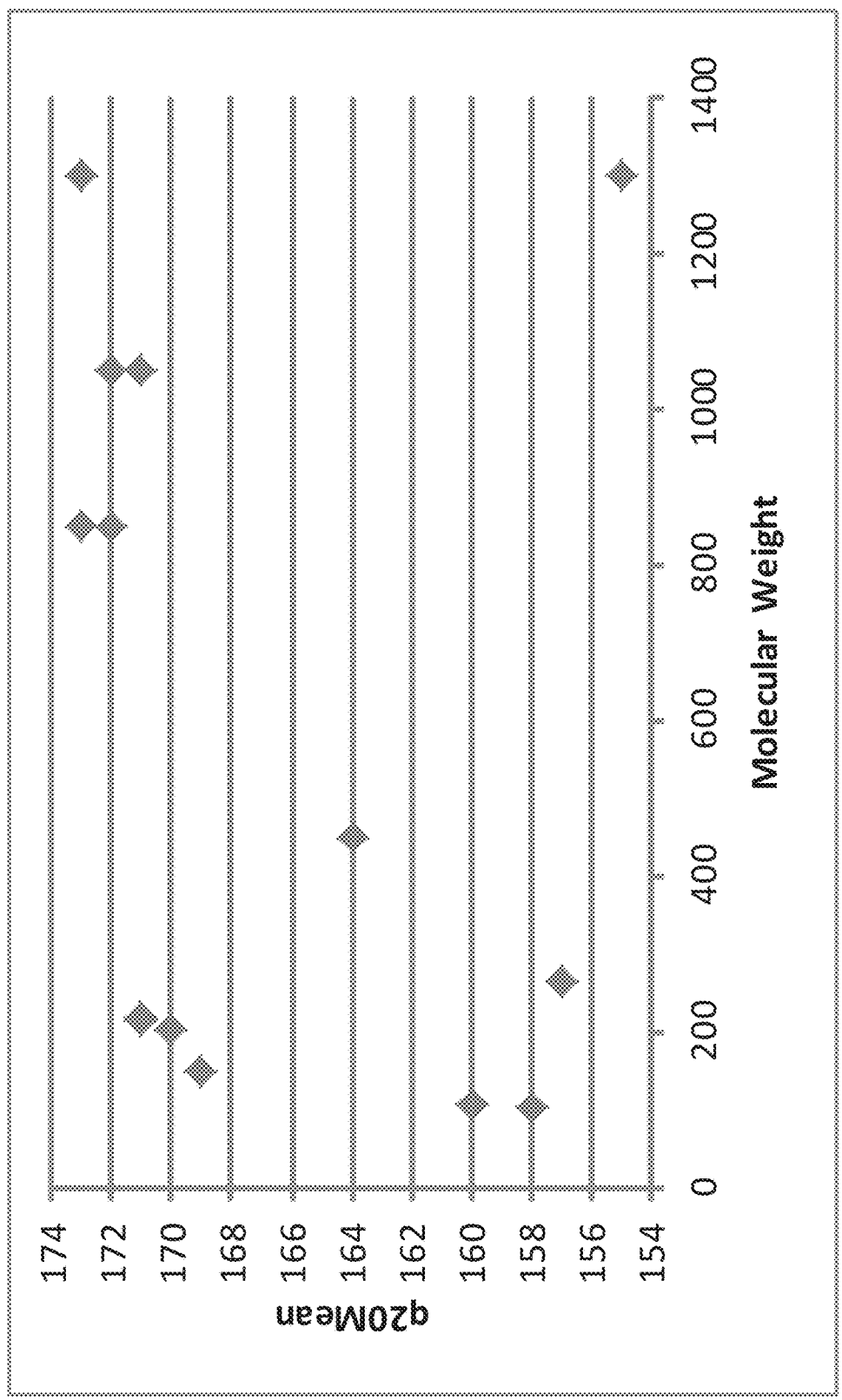

When utilized on a sequencing platform, the organo-silicon compounds provide for improved sequencing as indicated by q20 mean and illustrated in FIG. 16. In particular, several higher molecular weight PDMS species provide significantly improved q20 mean.

Example 2

Organo-silicon compounds selected from non-functionalized PDMS having molecular weight of 750 Da, 900 Da, 1200 Da, 2000 Da, 3700 Da, or 6000 Da are tested for influence on buffering, signal-to-noise, key signal, and q20 mean using an ION Torrent® Proton I on an ION Torrent® Proton Sequencer. A solution of undecane including 5 wt % dodecyl benzene sulfonic acid and 5 wt % of the selected organo-silicon compound are applied through ports of a Proton I chip and remain in contact with sensor surfaces for approximately 2 minutes. The Proton I chip is flushed with water and isopropyl alcohol. A 5 wt % DBSA in undecane solution is applied through port of the Proton I chip followed by a base solution including 10 mM NaOH. The DBSA and NaOH treatment is repeated three times. The Proton I chip is then flushed with water and isopropyl alcohol. A control is formed using three DBSA and NaOH treatments without exposure to an organo-silicon compound.

The Proton I chip is loaded with nucleic acid beads using an ION Chef under standard protocols. The Proton I chip is applied to the Proton Sequencer and standard testing is performed to determine buffering, loading, signal-to-noise, key signal, and q20 mean measurements.

TABLE

Effect of PDMS on Performance

| MW PDMS | Buffering | Loading (%) | q20mean |
|---|---|---|---|
| Control | 88 | | |
| 750 | 71 | 90.0 | 163.0 |
| 900 | 69 | 89.7 | 165.0 |
| 1200 | 68 | 90.6 | 169.0 |
| 2000 | 67 | 90.2 | 171.0 |
| 3700 | 70 | | |
| 6000 | 64 | | |

Each of the PDMS treated Proton I chips exhibit improved buffering and q20mean relative to the control chip. In addition, lower buffering and improved q20mean generally follows increased PDMS molecular weight.

Example 3

A solution of undecane including 5 wt % PDMS is applied through ports of a Proton I chip and remains in contact with sensor surfaces for approximately 1 minute. A second solution including undecane and 5 wt % DBSA is applied through ports of a Proton I chip, flushing at least a portion of the first solution from the chip, and remains in contact with sensor surfaces for approximately 2 minute. The Proton I chip is flushed with water and isopropyl alcohol. A base solution including 10 mM NaOH is applied for 60 seconds. The DBSA and NaOH treatment is repeated three times. The Proton I chip is then flushed with water and isopropyl alcohol.

The Proton I chip is loaded with nucleic acid beads using an ION Chef under standard protocols. The Proton I chip is applied to the Proton Sequencer and standard testing is performed to determine buffering, loading, signal-to-noise, key signal, and q20 mean measurements.

In a first aspect, a method of treating a sensor array including a plurality of sensors and an isolation structure, where a sensor of the plurality of sensors has a sensor pad exposed at a surface of the sensor array and the isolation structure is disposed between the sensor pad and sensor pads of other sensors of the plurality of sensors, comprises exposing the sensor pad and the isolation structure to a non-aqueous organo-silicon solution including an organo-silicon compound and a first non-aqueous carrier; applying an acid solution including an organic acid and a second non-aqueous carrier to the sensor pad; and rinsing the acid solution from the sensor pad and the isolation structure.

In an example of the first aspect, a portion of the organo-silicon compound remains on the isolation structure.

In another example of the first aspect and the above example, the organo-silicon compound includes a silane functionalized with an aryl, polyaryl, alkyl, alkoxy, halo, or cyano moiety, or any combination thereof. For example, the silane is selected from the group consisting of phenyldimethylchlorosilane, tert-butylchlorodiiphenylsilane, chlorotripropylsilane, (N,N-dimethylamino) trimethyl-silane, tris(trimethylsilyl)silane, triethylchlorosilane, 3-cyanopropyldimethylchloro-silane, chlorotriethylsilane, 1,2-bis(chlorodimethylsiyl)ethane, trimethylsilyltrifluoronesulfonate, trioctylsilane, dodecyldimethylchlorosilane, chlorodimethylthexylsilane, trimethylchlorosilane, chloro(chloromethyl) dimethylsilane, thexyldimethylchlorosilane, triisopropylchlorosilane, trimethylmethoxysilane, trimethylchlorosilane, chlorotriisopropylsilane, acetoxytrimethylsilane, and a combination thereof.

In a further example of the first aspect and the above example, the organo-silicon compound includes a polysiloxane including aryl, dialkyl or alkylhydro units, or combinations thereof. For example, the aryl unit includes a phenylalkyl siloxyl unit. In an example, the dilkyl unit or the alkylhydro unit includes an alkyl moiety selected from methyl, ethyl, propyl, butyl moieties, and a combination thereof. In a further example, the organo-silicon compound include a siloxane selected from the group consisting of an alkyl terminated polydimethylsiloxane, a hydride-terminated polydimethylsiloxane, a monovinyl terminated polydimethylsiloxane, dichloro-tetramethyldisiloxane, hexamethyltrisiloxane, polymethylhydrosiloxane, tris(trimethylsilyloxy)silane, octamethyltrisiloxane, and a combination thereof.

In an additional example of the first aspect and the above example, the organo-silicon compound includes a silazane.

In another example of the first aspect and the above example, the organo-silicon compound has a molecular weight in a range of 50 Da to 10000 Da. For example, the molecular weight is in a range of 100 Da to 8000 Da. In a further example, the molecular weight is in a range of 500 Da to 7000 Da.

In a further example of the first aspect and the above example, the organo-silicon solution includes the organo-silicon compound in an amount of 0.001% to 10.0% by weight. For example, the amount is in a range of 0.005% to 5.0% by weight.

In an additional example of the first aspect and the above example, the organo-silicon solution further includes a platinum compound.

In another example of the first aspect and the above example, the organic acid includes sulfonic acid. For example, the sulfonic acid includes alkyl sulfonic acid, alkyl aryl sulfonic acid, or a combination thereof. In an example, the alkyl aryl sulfonic acid includes an alkyl group having between 1 and 20 carbons. In another example, the sulfonic acid includes dodecyl benzene sulfonic acid.

In a further example of the first aspect and the above example, the treatment solution includes between 0.5 wt % and 25 wt % of the organic acid.

In an additional example of the first aspect and the above example, the first or second non-aqueous carrier is non-polar.

In another example of the first aspect and the above example, the first or second non-aqueous carrier has a normal boiling point in a range of 36° C. to 345° C.

In a further example of the first aspect and the above example, the first or second non-aqueous carrier is an alkane having between 6 and 24 carbons.

In an additional example of the first aspect and the above example, the method further includes heating the sensor pad, the isolation structure, and the treatment solution while exposing the sensor pad to the treatment solution. For example, heating includes heating at a temperature in a range of 35° C. to 70° C.

In another example of the first aspect and the above example, exposing includes exposing for a period in a range of 30 seconds to 30 minutes.

In a further example of the first aspect and the above example, the method further includes exposing at least the sensor pad to a basic solution. For example, the basic solution includes between 0.005M and 1.5M sodium hydroxide. In another example, exposing at least the sensor pad to the basic solution occurs following exposing the sensor pad to the treatment solution. In a further example, the method further includes repeating exposing at least the sensor pad to the acid solution and exposing at least the sensor pad to the basic solution.

In an additional example of the first aspect and the above example, rinsing includes rinsing with a rinse organic solvent miscible with water and the first or second non-aqueous carrier.

In another example of the first aspect and the above example, rinsing includes rinsing with a low boiling organic solvent having a normal boiling point in a range of 25° C. to 100° C. In an example, the low boiling organic solvent includes alcohol.

In a further example of the first aspect and the above example, rinsing includes rinsing with water.

In a second aspect, a method of treating a sensor array including a plurality of sensors and an isolation structure, wherein a sensor of the plurality of sensors has a sensor pad exposed at a surface of the sensor array and the isolation structure is disposed between the sensor pad and sensor pads of other sensors of the plurality of sensors, comprises exposing at least the sensor pad and the isolation structure to a treatment solution including an organo-silicon compound, an organic acid, and an organic solvent; and rinsing the treatment solution from the sensor pad.

In an example of the second aspect, the organo-silicon compound includes a silane functionalized with an aryl, polyaryl, alkyl, alkoxy, halo, or cyano moiety, or any combination thereof. For example, the silane is selected from the group consisting of phenyldimethylchlorosilane, tert-butyl-chlorodiiphenylsilane, chlorotripropylsilane, (N,N-dimethylamino) trimethyl-silane, tris(trimethylsilyl)silane, triethylchlorosilane, 3-cyanopropyldimethylchloro-silane, chlorotriethylsilane, 1,2-bis(chlorodimethylsiyl)ethane, trimethylsilyltrifluoronesulfonate, trioctylsilane, dodecyldimethylchlorosilane, chlorodimethylthexylsilane, trimethylchlorosilane, chloro(chloromethyl) dimethylsilane, thexyldimethylchlorosilane, triisopropylchlorosilane, trimethylmethoxysilane, trimethylchlorosilane, chlorotriisopropylsilane, acetoxytrimethylsilane, and a combination thereof.

In another example of the second aspect and the above example, the organo-silicon compound includes a polysiloxane including aryl, dialkyl or alkylhydro units, or combinations thereof. For example, the aryl unit includes a phenylalkyl siloxyl unit. In an example, the dilkyl unit or the alkylhydro unit includes an alkyl moiety selected from methyl, ethyl, propyl, butyl moieties, and a combination thereof. In another example, the organo-silicon compound include a siloxane selected from the group consisting of an alkyl terminated polydimethylsiloxane, a hydride-terminated polydimethylsiloxane, a monovinyl terminated polydimethylsiloxane, dichloro-tetramethyldisiloxane, hexamethyltrisiloxane, polymethylhydrosiloxane, tris (trimethylsilyloxy)silane, octamethyltrisiloxane, and a combination thereof.

In a further example of the second aspect and the above example, the organo-silicon compound includes a silazane.

In an additional example of the second aspect and the above example, the organo-silicon compound has a molecular weight in a range of 50 Da to 10000 Da. In an example, the molecular weight is in a range of 100 Da to 8000 Da. For example, the molecular weight is in a range of 500 Da to 7000 Da.

In another example of the second aspect and the above example, the treatment solution includes the organo-silicon compound in an amount of 0.001% to 10.0% by weight. For example, the amount is in a range of 0.005% to 5.0% by weight.

In a further example of the second aspect and the above example, the treatment solution further includes a platinum compound.

In an additional example of the second aspect and the above example, the acid includes sulfonic acid. In an example, the sulfonic acid includes alkyl sulfonic acid, alkyl aryl sulfonic acid, or a combination thereof. For example, the alkyl aryl sulfonic acid includes an alkyl group having between 1 and 20 carbons.

In another example of the second aspect and the above example, the sulfonic acid includes dodecyl benzene sulfonic acid.

In a further example of the second aspect and the above example, the treatment solution includes between 0.5 wt % and 25 wt % of the acid.

In an additional example of the second aspect and the above example, the organic solvent is non-polar.

In another example of the second aspect and the above example, the organic solvent has a normal boiling point in a range of 36° C. to 345° C.

In a further example of the second aspect and the above example, the organic solvent is an alkane having between 6 and 24 carbons.

In an additional example of the second aspect and the above example, the method further includes heating the sensor pad and the treatment solution while exposing the sensor pad to the treatment solution. For example, heating includes heating at a temperature in a range of 35° C. to 70° C.

In another example of the second aspect and the above example, exposing includes exposing for a period in a range of 30 seconds to 30 minutes.

In a further example of the second aspect and the above example, the method further includes exposing at least the sensor pad to a basic solution. In an example, the basic solution includes between 0.005M and 1.5M sodium hydroxide. For example, exposing at least the sensor pad to the basic solution occurs following exposing the sensor pad to the treatment solution. In an another example, the method further includes repeating exposing at least the sensor pad to the treatment solution and exposing at least the sensor pad to the basic solution.

In an additional example of the second aspect and the above example, rinsing includes rinsing with a rinse organic solvent miscible with water and the organic solvent.

In another example of the second aspect and the above example, rinsing includes rinsing with a low boiling organic solvent having a normal boiling point in a range of 25° C. to 100° C. For example, the low boiling organic solvent includes alcohol.

In a further example of the second aspect and the above example, rinsing includes rinsing with water.

In a third aspect, a method of treating a sensor array including a plurality of sensors, wherein a sensor of the plurality of the sensors includes a sensor pad, a well structure defines a well array corresponding with the sensor array, a well of the well array exposes the sensor pad, a lid is attached over the sensor array and the well structure and including an fluid port, and a space is defined between the lid and the well structure, comprises applying a treatment solution through the fluid port into the space and waiting for a first period between 30 seconds and 30 minutes, the treatment solution including an organo-silicon compound, an acid and an organic solvent; applying a basic solution through the fluid port into the space and waiting for a second period between 20 seconds and 15 minutes; and applying a rinse solution through the fluid port.

In an example of the third aspect, the method further includes repeating applying the treatment solution, applying the basic solution, and applying the rinse solution.

In a fourth aspect, a method of treating a sensor array including a plurality of sensors, wherein a sensor of the plurality of the sensors includes a sensor pad, a well structure defines a well array corresponding with the sensor array, and a well of the well array exposes the sensor pad, comprises applying a treatment solution to at least the sensor pad and waiting for a first period between 30 seconds and 30 minutes, the treatment solution including an organo-silicon compound, an acid and an organic solvent; rinsing at least the sensor pad with a low boiling organic solvent; and drying the sensor array.

In an example of the fourth aspect, the method further includes rinsing with water following rinsing with the low boiling organic solvent and prior to drying.

In another example of the fourth aspect and the above example, the method further includes attaching a lid over the sensor array and the well array, the lid including a fluid port, a space defined between the lid and the well array in fluid communication with the fluid port.

In a fifth aspect, a sensor device is treated by the method of any one of the above aspects and examples.

In a sixth aspect, a solution includes 0.001 wt % to 10.0 wt % of an organo-silicon compound, 2.5 wt % to 5 wt % dodecyl benzene sulfonic acid and a non-polar linear alkane having between 6 and 18 carbons.

In a seventh aspect, a kit includes a nucleotide solution including at least one nucleotide type; polymeric particles; and a treatment solution including 0.001 wt % to 10.0 wt % of an organo-silicon compound, 0.5 wt % to 20 wt % sulfonic acid and an organic solvent having a normal boiling point in a range of 65° C. to 275° C.

In a further example of the above aspects and examples, the organo-silicon compound includes a polysiloxane including hydrophilic, polar, or amphiphilic units, or combinations thereof.

Note that not all of the activities described above in the general description or the examples are required, that a portion of a specific activity may not be required, and that one or more further activities may be performed in addition to those described. Still further, the order in which activities are listed are not necessarily the order in which they are performed.

Particular salts of above described acids or bases can have activity, and may be useful in the above described methods. Salts include alkali or alkali earth metal salts, or tetraalkylammonium salts of the above acids or bases.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of treating a sensor array, the sensor array including a plurality of sensors, a sensor of the plurality of the sensors including a sensor pad, a well structure defining a well array having a plurality of wells, a well of the plurality of wells disposed over each sensor of the sensor array and providing an opening to the sensor pad, a lid attached over the sensor array and the well structure and including a fluid port, a space defined between the lid and the well structure, the method comprising:

applying a treatment solution through the fluid port into the space and waiting for a first period between 30 seconds and 30 minutes, the treatment solution entering the well and contacting the sensor pad, the treatment solution including an organo-silicon compound, an organic acid and an organic solvent, the organic solvent has a normal boiling point in a range of 36° C. to 345° C.;

applying a basic solution through the fluid port into the space and waiting for a second period between 20 seconds and 15 minutes, the basic solution entering the well and contacting the sensor pad; and applying a rinse solution through the fluid port the rinse solution entering the well and contacting the sensor pad.

2. The method of claim 1, wherein the organo-silicon compound includes a silane functionalized with an aryl, polyaryl, alkyl, alkoxy, halo, or cyano moiety, or any combination thereof.

3. The method of claim 1, wherein the organo-silicon compound includes a polysiloxane including aryl, dialkyl or alkylhydro units, or combinations thereof.

4. The method of claim 1, wherein the organo-silicon compound includes a siloxane selected from the group consisting of an alkyl terminated polydimethylsiloxane, a hydride-terminated polydimethylsiloxane, a monovinyl terminated polydimethylsiloxane, dichloro-tetramethyldisiloxane, hexamethyltrisiloxane, polymethylhydrosiloxane, tris(trimethylsilyloxy)silane, octamethyltrisiloxane, and a combination thereof.

5. The method of claim 1, wherein the organo-silicon compound has a molecular weight in a range of 50 Da to 10000 Da.

6. The method of claim 1, wherein the treatment solution includes the organo-silicon compound in an amount of 0.001% to 10.0% by weight.

7. The method of claim 1, wherein the treatment solution further includes a platinum compound.

8. The method of claim 1, wherein the organic acid includes sulfonic acid.

9. The method of claim 1, wherein the treatment solution includes between 0.5 wt % and 25 wt % of the organic acid.

10. The method of claim 1, wherein the organic solvent is non-polar.

11. The method of claim 1, wherein the organic solvent has a normal boiling point in a range of 65° C. to 275° C.

12. The method of claim 1, further comprising heating the sensor pad and the treatment solution while exposing the sensor pad to the treatment solution, wherein heating includes heating at a temperature in a range of 35° C. to 70° C.

13. The method of claim 1, wherein the basic solution includes between 0.005M and 1.5M sodium hydroxide.

14. The method of claim 1, further comprising repeating exposing at least the sensor pad to the treatment solution and exposing at least the sensor pad to the basic solution.

15. The method of claim 14, further comprising repeating applying the treatment solution, applying the basic solution, and applying the rinse solution.

16. The method of claim 2, wherein the silane is selected from the group consisting of phenyldimethylchlorosilane, tert-butylchlorodiiphenylsilane, chlorotripropylsilane, (N,N-dimethylamino) trimethyl-silane, tris(trimethylsilyl)silane, triethylchlorosilane, 3-cyanopropyldimethylchlorosilane, chlorotriethylsilane, 1,2-bis(chlorodimethylsiyl)ethane, trimethylsilyltrifluoronesulfonate, trioctylsilane, dodecyldimethylchlorosilane, chlorodimethylthexylsilane, trimethylchlorosilane, chloro(chloromethyl) dimethylsilane, thexyldimethylchlorosilane, triisopropylchlorosilane, trimethylmethoxysilane, trimethylchlorosilane, chlorotriisopropylsilane, acetoxytrimethylsilane, and a combination thereof.

17. The method of claim 8, wherein the sulfonic acid includes alkyl sulfonic acid, alkyl aryl sulfonic acid, or a combination thereof.

18. The method of claim 13, wherein exposing at least the sensor pad to the basic solution occurs following exposing the sensor pad to the treatment solution.

19. The method of claim 17, wherein the alkyl aryl sulfonic acid includes an alkyl group having between 1 and 20 carbons.

* * * * *